United States Patent
Sørensen et al.

(10) Patent No.: US 11,069,064 B2
(45) Date of Patent: Jul. 20, 2021

(54) METHOD AND SYSTEM FOR MODELLING A HUMAN HEART AND ATRIA

(71) Applicant: MEDTRACE PHARMA A/S, Kongens Lyngby (DK)

(72) Inventors: Jens Sørensen, Uppsala (SE); Hendrik Johannes Harms, Brookline, MA (US)

(73) Assignee: MEDTRACE PHARMA A/S, Kongens Lyngby (DK)

( * ) Notice: Subject to any disclaimer, the term of this patent is extended or adjusted under 35 U.S.C. 154(b) by 85 days.

(21) Appl. No.: 16/349,238

(22) PCT Filed: Nov. 10, 2017

(86) PCT No.: PCT/DK2017/050367
§ 371 (c)(1),
(2) Date: May 10, 2019

(87) PCT Pub. No.: WO2018/086667
PCT Pub. Date: May 17, 2018

(65) Prior Publication Data
US 2019/0279364 A1    Sep. 12, 2019

(30) Foreign Application Priority Data
Nov. 11, 2016  (DK) .......................... PA 2016 70895

(51) Int. Cl.
*G06T 7/00*     (2017.01)
*A61B 6/03*     (2006.01)
(Continued)

(52) U.S. Cl.
CPC ............ *G06T 7/0016* (2013.01); *A61B 6/037* (2013.01); *A61B 6/481* (2013.01); *A61B 6/486* (2013.01);
(Continued)

(58) Field of Classification Search
CPC ................... G06T 7/0016; G06T 15/08; G06T 2207/10076; G06T 2207/10104;
(Continued)

(56) References Cited

U.S. PATENT DOCUMENTS 5,526,817 A * 6/1996 Pfeiffer .................. A61B 5/028
                                                          600/481
6,856,836 B2 * 2/2005 Ding .................... A61N 1/3627
                                                          607/17
(Continued)

OTHER PUBLICATIONS

Koh, "Left atrial enlargement increases the 30 risk of major adverse cardiac events independent of coronary vasodilator capacity" European Journal on Nuclear Medicine May 2015.*
(Continued)

*Primary Examiner* — Juan A Torres
(74) *Attorney, Agent, or Firm* — Quarles & Brady LLP

(57) ABSTRACT

A method and a system for modelling a human heart based on a plurality of emission tomography images representing concentrations of a tracer that has been injected at a specific time is presented. The method comprising: extracting time activity curves of a tracer that has been injected for a plurality of pixels and/or voxels; identifying first-pass peaks of the time activity curves corresponding to an arrival time of the injected tracer at the corresponding pixel/voxel; defining a model comprising at least two portions of the heart; and arranging the at least two portions in relation to each other by comparing the arrival times of the first-pass peaks. The method and model may be used to obtain an estimate of the volume of the left or right atrium of the human heart.

24 Claims, 15 Drawing Sheets

(51) Int. Cl.
*A61B 6/00* (2006.01)
*G06T 15/08* (2011.01)
*A61B 5/029* (2006.01)
*A61B 5/0275* (2006.01)

(52) U.S. Cl.
CPC .............. *A61B 6/503* (2013.01); *A61B 6/507* (2013.01); *A61B 6/5205* (2013.01); *G06T 15/08* (2013.01); *A61B 5/029* (2013.01); *A61B 5/02755* (2013.01); *G06T 2207/10076* (2013.01); *G06T 2207/10104* (2013.01); *G06T 2207/30048* (2013.01); *G06T 2207/30101* (2013.01); *G06T 2210/41* (2013.01)

(58) Field of Classification Search
CPC . G06T 2207/30048; G06T 2207/30101; G06T 2210/41; A61B 6/486; A61B 6/507; A61B 6/037; A61B 6/481; A61B 6/503; A61B 6/5205; A61B 5/029; A61B 5/02755
USPC ........................................................ 382/131
See application file for complete search history.

(56) References Cited

U.S. PATENT DOCUMENTS

| | | | | |
|---|---|---|---|---|
| 7,314,449 B2* | 1/2008 | Pfeiffer | .............. | A61B 5/02028 600/481 |
| 7,402,134 B2* | 7/2008 | Moaddeb | .............. | A61F 2/2478 600/37 |
| 7,650,021 B2* | 1/2010 | Braess | .................. | A61B 6/481 382/128 |
| 8,103,070 B2* | 1/2012 | Roberts | .................. | G06T 19/00 382/128 |
| 2010/0168554 A1* | 7/2010 | Sorensen | ............... | A61B 6/504 600/420 |
| 2011/0150309 A1 | 6/2011 | Barfett et al. | | |
| 2014/0163403 A1* | 6/2014 | Lenox | .................. | A61B 5/7235 600/504 |

OTHER PUBLICATIONS

Harms, "Automatic generation of absolute myocardial blood flow images using 15O-H2O and a clinical PET/CT scanner" European Journal on Nuclear Medicine Year 2011.*

Harms "Automatic Extraction of Myocardial Mass and Volume Using Parametric Images from Dynamic Nongated PET". The Journal on Nuclear Medicine Year 2016.*

Harms, Hendrik Johannes, et al., Automatic Extraction of Myocardial Mass and Volume Using Parametric Images from Dynamic Nongated PET, J Nuclear Med, vol. 57, No. 9, Sep. 2016, pp. 1382-1387.

International Search Report and Written Opinion of PCT/DK2017/050367 (dated Feb. 8, 2018).

* cited by examiner

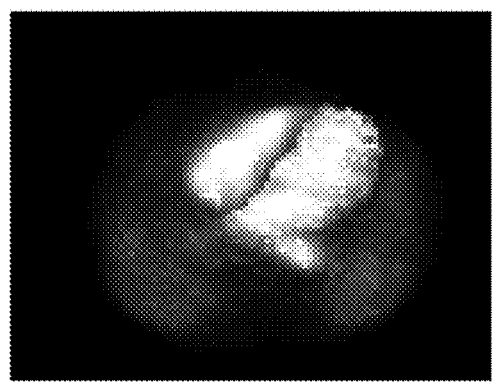 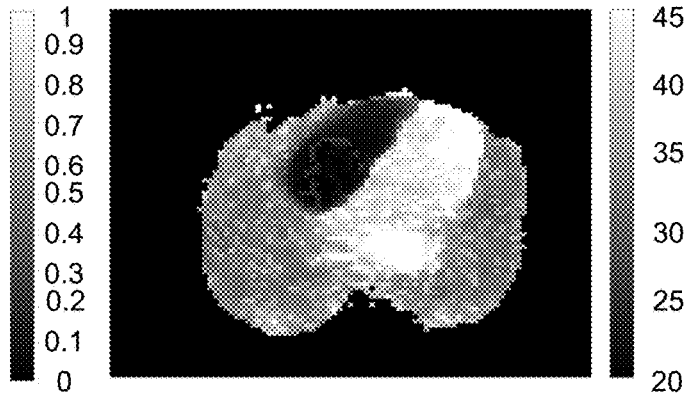
FIG. 5A                FIG. 5B
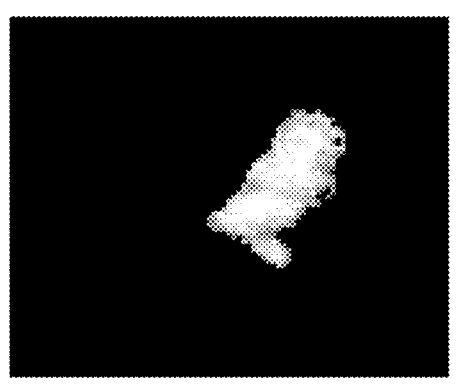 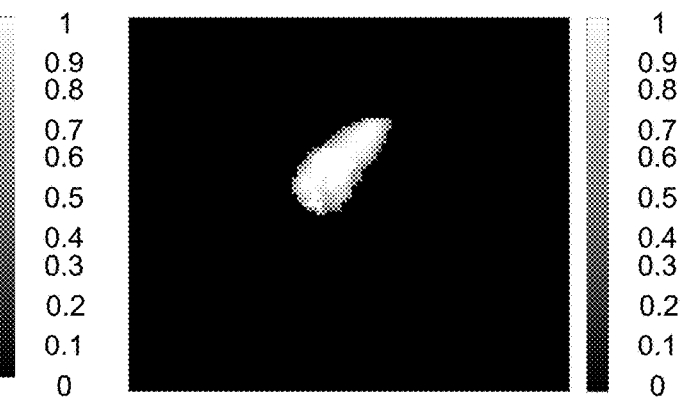
FIG. 6A                FIG. 6B

METHOD AND SYSTEM FOR MODELLING A HUMAN HEART AND ATRIA

CROSS-REFERENCE TO RELATED APPLICATIONS

This patent application is a national stage filing under 35 U.S.C. 371 of International Application No. PCT/DK2017/050367, filed Nov. 10, 2017, which claims the benefit of priority of Danish Patent Application No. PA 2016 70895, filed Nov. 11, 2016, each of which are incorporated herein by reference in their entirety.

FIELD OF THE INVENTION

The present disclosure relates to a method and system for modelling a human heart, and/or chambers and cavities therein, such as the left and right atrium, based on emission tomography images. The disclosure further relates to identification of conditions based on the model.

BACKGROUND OF INVENTION

Positron emission tomography (PET) is an imaging technique that is used to observe metabolic processes in the body. The system detects gamma rays emitted indirectly by a positron-emitting radionuclide (tracer), which is introduced into the body. Three-dimensional images of tracer concentration within the body are then constructed by computer analysis. In modem scanners, three dimensional imaging is accomplished with the aid of a computed tomography (CT) X-ray scan performed on the patient during the same session, in the same machine.

PET is increasingly used to quantify the blood flow in the heart muscle itself. The blood flow is an important prognostic and diagnostic marker in heart disease. [$^{15}$O] labeled water has been used to obtain blood flow from PET. Multiple publications show that [$^{15}$O]H$_2$O ($^{15}$O-water) is an accurate way of obtaining blood flow in PET scanning. It is known how to calculate this blood flow.

However, blood flow is not the sole factor in heart disease or cardiac diagnostics. It is common that, in addition to blood flow calculations, further clinical examinations are required to obtain for example the stroke volume of the heart, the dimensions of the heart and the pressures during filling and contraction of the heart and other parameters. Such examination may include for example magnetic resonance imaging (MRI).

The left atrium (LA) is one of the four cavities of the heart and functions as a reservoir for blood passing from the lungs to the left ventricle and further into aortic blood stream. The filling pattern of the LA consists of a filling phase and a contractive phase. Filling and contraction normally work seamlessly in order to minimize resistance to blood flowing from the lung veins to the left ventricle. In the normal heart, the LA volume (LAV) cyclically changes by 30% during one heartbeat. Normally, the LAV is 40-60 milliliter when maximal volume is reached. Because LAV varies physiologically with body size, the volume is generally indexed by normalization to body area (m$^2$). A normal LAVI typically does not exceed 34 mL/m$^2$.

LAV tends to increase whenever there is resistance to left ventricular filling, which might occur in connection with a variety of cardiac diseases such as myocardial ischemia, hypertrophy, diastolic or systolic heart failure. Besides, diseases directly affecting the LA, such as atrial fibrillation or atrial degeneration might lead to dilatation. Increased LAV is a powerful prognostic indicator and measurement is recommended in numerous state-of-the-art guidelines.

The most common method for measuring LAV is echocardiography. Typically, the LAV is then approximated by a geometric equation based on a standardized LA area.

Because LA configuration is highly variable, the conversion of area to volume is subject to measurement error and observer bias. Direct three-dimensional measurements of LA are possible using specialized equipment, but is rarely performed in clinical routine. The gold standard for measuring LAV is currently a cardiac magnetic resonance tomographic imaging (CMR) technique, where the LA is imaged with thin sections in which the blood pool is outlined using manual planimetry for each slice. Even with CMR the 3D technique is not routinely used, mainly because this requires additional scanning- and labour time. Instead, the LAV is routinely approximated by measuring a cross-sectional area within a standardized 2D view through all four chambers.

The LA volume is thus a marker of cardiovascular risk independent of myocardial blood flow (MBF), and assessing both parameters simultaneously rather than by separate examinations would improve the quality of risk stratification. The prognostic value of left-atrial enlargement alone has been shown unequivocally. However, to date only a single study has integrated fully quantitative myocardial perfusion imaging and left atrial enlargement as prognostic marker [Koh A S et al. Left atrial enlargement increases the risk of major adverse cardiac events independent of coronary vasodilator capacity. Eur J Nucl Med Mollmaging. 2015; 42:1551-61]. In that study, left-atrial enlargement was an independent predictor of cardiac events, with a 2.7-fold increase in risk in the entire population and most notably a 5.4-fold increase in patients with a preserved flow reserve. The methods employed in this study were however completely manual, and to some degree observer-dependent, complicating efforts to integrate measures of MBF and LA volumes in a standard workflow.

Deriving LA volume from PET data is thus known to be labour intensive and prone to observer variation. There is therefore a demand for a method which can measure the left atrial (LA) volume and the myocardial blood flow (MBF) in a single operation.

As another cardiac disease example can be mentioned pulmonary congestion, which is an important finding in heart failure (HF) and relates to prognosis. Currently pulmonary congestion can be evaluated invasively by transpulmonary thermodilution measuring extravascular lung water content (EVLW) and preload by global end-diastolic volume (GEDV) by the PICCO (pulse indexed contour cardiac output) device and from invasive pulmonary wedge pressure (PCWP). However, at present, no reliable non-invasive methods are available for quantitatively measuring EVLW and preloading. There is therefore also a demand for a method which can estimate pulmonary congestion and preload quantitatively without resorting to invasive methods.

SUMMARY OF INVENTION

The present disclosure relates to a method for modelling a human heart and/or chambers and cavities therein, such as the left and right atrium, or a human central circulation comprising a human heart, based on PET images, which addresses many of the issues involved with the currently employed diagnostic methods used in connection with cardiac diseases, or suspicion thereof.

The method as disclosed in certain embodiments is particularly suitable for estimating the volume of individual chambers, cavities, or atria of the human heart.

By segmenting the various chambers and large vessels in the central circulation, a segmented model is obtained, from which further parameters and information can be obtained. The method may be used for example in, or carried out by computer software programs for analysis of dynamic PET scans of the heart.

The invention thus in a general sense relates to a method for modelling a human heart and/or chambers and cavities therein, such as the left and right atrium, based on a plurality of emission tomography images, such as positron emission tomography (PET) and single-photon emission computed tomography (SPECT) images of said human heart, wherein each image represents concentrations of a tracer that has been injected at a specific time, the method comprising the steps of:

A. extracting time activity curves of a tracer that has been injected for a plurality of pixels and/or voxels;
B. isolating first-pass peaks of the time activity curves, each peak corresponding to an arrival time of the injected tracer at the corresponding pixel/voxel;
C. defining a model comprising at least two portions of the heart, wherein the at least two portions are isolated by selecting pixels and/or voxels based on comparisons of the first-pass peaks against a threshold;
D. arranging the at least two portions in relation to each other by comparing the arrival times of the first-pass peaks of the pixels and/or voxels in the portions, thereby obtaining a segmented model of the human heart.

Preferably, the steps are sequential. The method may in a specific embodiment be used to obtain an estimate of the volume of the left or right atrium of said human heart.

One particular purpose of the invention is to segment the various chambers and large vessels in the central circulation (such as the heart, including the left and right atrium, the lungs and the pulmonary vessels). From this segmentation, additional analyses can then be performed on for example the volumes of each region or the PET activity over time of regions or sub-regions, yielding transit times of small sub-regions of the central circulation. The method may be integrated in a software program used for standard analysis of dynamic PET scans of the heart. The disclosed methods may be used to overcome the need for additional clinical examinations of the heart by modelling a human heart and/or chambers and cavities therein, such as the left and right atrium, such that functional parameters can be obtained from the same $^{15}$O-water PET scan that is conventionally performed for measuring cardiac blood flow. The model of the human heart may be a three-dimensional model. The method may be directed specifically to an estimation of the left or right atrium of the human heart.

The segmentation may be performed such that first-pass peaks for a number of tracer concentration curves over time are identified and, in a first step, a region is identified based on a map of intensities. The boundaries of a region are achieved by including pixels having intensities over a certain predefined level and excluding pixels below the level. Once at least two portions (regions) have been established, the arrival times of the peaks are used to arrange the portions in a sequence. With reference to a known sequential model of the heart, wherein the blood passes through a number of regions in a known sequence, a segmented model can be built in steps.

Reference points may be selected from the plurality of pixels and/or voxels, the reference points corresponding to reference points in the human heart. By iteratively repeating steps C-D the model may be further divided into sub-portions (step C), wherein the sub-portions are arranged in relation to each other by comparing the arrival times of their first-pass peaks (step D), thereby further segmenting the model of the human heart and/or chambers and cavities therein, such as the left and right atrium. This may be used to obtain a representation of a number of regions of the heart, such as the Vena Cava (VC), Right Atrium (RA), Right Ventricle (RV), the base of the Pulmonary Artery (PA), the Pulmonary Veins (PV) close to the left atrium, the Left Atrium (LA) itself, the Left Ventricle (LV) and the base of the Ascending Aorta (AA).

The presently disclosed, general method for modelling a human heart and/or chambers and cavities therein, such as the left and right atrium, may be used for a number of specific purposes. One further method of the present disclosure relates to identifying a cardiac disease by analyzing the volumes of the sub-portions of the segmented model obtained in the method for modelling a human heart according to the present disclosure. The disclosure further relates to a method for identifying a preloading condition of a patient based on an end-diastolic volume, wherein said end-diastolic volume is the volume of the right portion or the left portion of the heart obtained in the method for modelling a human heart, and a method for identifying leakage of a cardiac valve, based on a segmented model obtained in the method for modelling a human heart, a forward stroke volume and a forward cardiac output of the left ventricle.

The present inventors have inter alia found that the left atrium (LA) and right atrium (RA) can both be segmented automatically using images of bolus area-under-curve and midpoint time. For example, using the midpoint time of the left-ventricular (LV) cavity as reference, the LA can be segmented as regions with high first-pass activity and a midpoint time shorter than that of the LV. The RA can be segmented automatically in a similar fashion.

The present invention includes, without limitation, the following objects:

One object is a method for modelling a human heart based on a plurality of emission tomography images, such as positron emission tomography images or single-photon emission computed tomography images, of said human heart, wherein each image represents concentrations of a tracer that has been injected at a specific time, the method comprising the steps of:

A. extracting time activity curves, of the tracer that has been injected, for a plurality of pixels and/or voxels;
B. identifying first-pass peaks of the time activity curves, each peak corresponding to an arrival time of the injected tracer at the corresponding pixel/voxel;
C. defining a model comprising at least two portions of the heart, wherein the at least two portions are isolated by selecting pixels and/or voxels based on comparisons of the first-pass peaks against a threshold; and
D. arranging the at least two portions in relation to each other by comparing the arrival times of the first-pass peaks of the pixels and/or voxels in the portions, thereby obtaining a segmented model of the human heart.

In some embodiments, a first portion of said two portions is a left portion of the heart and the second portion of said two portions is a right portion of the heart.

In some embodiments, reference points of the human heart are selected from the plurality of pixels and/or voxels.

In some embodiments, steps C-D are iteratively repeated by dividing one or more of the at least two portions further into sub-portions (step C) and arranging the sub-portions in relation to each other by comparing the arrival times of their first-pass peaks (step D), thereby further segmenting the model of the human heart.

In some embodiments, each reference point corresponds to a chamber or vessel of the heart.

In some embodiments, the chambers are selected from the right atrium, the right ventricle, the left atrium and the left ventricle of the heart.

In some embodiments, the at least two portions correspond to chambers and large vessels of the heart selected from the vena cava, the right atrium, the right ventricle, the base of the pulmonary artery, the pulmonary veins close to the left atrium, the left atrium, the left ventricle and the base of the ascending aorta of the heart.

In some embodiments, the at least two portions, corresponding to chambers and large vessels of the heart, form a sequential flow model.

In some embodiments, the steps are sequential.

In some embodiments, the step of defining a model comprising at least two portions of the heart comprises the step of isolating the two portions from surrounding tissue.

In some embodiments, the tracer is $^{15}$O-water.

In some embodiments, the tracer has been injected in a vein entering the right atrium of the heart.

In some embodiments, the at least two portions are isolated by selecting pixels and/or voxels based on comparisons of the areas of the peaks against a threshold.

In some embodiments, the tracer that has been injected is a bolus of radio-opaque contrast media, wherein the first-pass peak of each time activity curves corresponds to the bolus arriving at the pixel/voxel.

In some embodiments, a center of mass in time is obtained for each of the time activity curves of the pixels/voxels.

In some embodiments, a transit time between two reference points of the portions and/or sub-portions is calculated.

In some embodiments, the transit time is calculated between a reference point at an entering boundary of the right portion of the heart and a reference point at an exiting boundary of the right portion of the heart, and/or between a reference point at an entering boundary of the lungs and a reference point at an exiting boundary of the lungs, and/or between a reference point at an entering boundary of the left portion of the heart and a reference point at an exiting boundary of the left portion of the heart.

In some embodiments, transit times are calculated between two or more sub-portions.

In some embodiments, the method further comprises the step of calculating volumes of the portions and/or sub-portions.

In some embodiments, the step of calculating volumes of the portions and/or sub-portions comprises the step of multiplying a transit time for a portion or sub-portion with a calculated cardiac output for the same portion/sub-portion.

In some embodiments, the model of the human heart is a three-dimensional model.

Another object is a method for identifying a cardiac disease by analyzing the volumes of the sub-portions of the segmented model obtained in the method for modelling a human heart according to any of the methods described herein.

Another object is a method for identifying a preloading condition of a patient based on an end-diastolic volume, wherein said end-diastolic volume is the volume of the right portion or the left portion of the heart obtained in the method for modelling a human heart according to any of methods described herein.

Another object is a method for identifying leakage of a cardiac valve based on a segmented model obtained in the method for modelling a human heart according to any of the methods described herein, a forward stroke volume and a forward cardiac output of the left ventricle.

Another object is a non-transitory computer readable storage medium containing computer executable instructions that, when executed by a processor, cause said processor to execute or perform any of the methods described herein.

Another object is a system for modelling a human heart based on a plurality of emission tomography images, such as positron emission tomography images or single-photon emission computed tomography images, of said human heart, said system being arranged to perform any of the methods described herein.

In some embodiments, system comprises an emission imaging device arranged to provide the emission tomography images and/or a processor arranged to perform the method for modelling a human heart.

In a first preferred embodiment the present invention thus relates to a method for estimating the volume of an atrium (left (LA) or right (RA)) based on a plurality of emission tomography images, such as positron emission tomography images or single-photon emission computed tomography images, which method will be described in detail in the detailed description.

The present inventors have further demonstrated that $^{15}$O—H$_2$O-PET can be used to estimate congestion and preload simultaneously and quantitatively by myocardial $^{15}$O—H$_2$O-PET using established transpulmonary dilution methods, that resembles those applied by pulse indexed contour cardiac output (PICCO).

In a second preferred embodiment the present invention thus relates to a method for quantitative estimation of extravascular lung water (EVLW) and preloading based on a plurality of emission tomography images, such as positron emission tomography images or single-photon emission computed tomography images, which method will be described in detail in the detailed description.

The steps of the first as well as the second preferred embodiment can conveniently be automated by employing a computing device comprising a computer readable storage medium containing instructions that, when executed by a processor, are configured to cause said computing device to execute or perform said method steps.

Definitions

The following abbreviations are used throughout the application:
AA: Ascending Aorta
ANOVA: ANalysis Of VAriance
AUC: area under curve
CAD: Coronary artery disease (CAD)
CFR: Coronary flow reserve
CMR: Cardiac magnetic resonance tomographic imaging
CO: Cardiac Output
CT: Computed tomography
CTT: Cardiac transit time
EVLW: Extravascular lung water content
GEDV: Global end-diastolic volume
HF: Heart failure
ITBV: Intrathoracic blood volume ITTV: Intrathoracic total volume
LA: Left atrium. LA is one of the four cavities of the heart and functions as a reservoir for blood passing from the lungs to the left ventricle and further into aortic blood stream.
LAL: LA length
LAV: LA volume. This cyclically changes by 30% during one heartbeat. Normally, the
LAV is 40-60 milliliter when maximal volume is reached.
LAVI: LA volume index
LGEDV: Left global end diastolic volume
LTT: Left heart Transit Time
LV: Left Ventricle
LVOT: Left-ventricular outflow tract
MBF: Myocardial blood flow
MRI: Magnetic resonance imaging
MVD: Microvascular dysfunction
PA: Pulmonary Artery
PAC: Pulmonary arterial catheterization
PV: Pulmonary Veins
PET: Positron emission tomography
PCWP: Pulmonary wedge pressure
PICCO: Pulse indexed contour cardiac output
PTF: Perfusable tissue fraction
PAP: Pulmonary artery pressure
PTT: Pulmonary Transit Time
PWV: Pulmonary water volume
RA: Right Atrium
RGEDV: Right global end diastolic volume
RTT: Right heart Transit Time
RV: Right Ventricle
SPECT: single-photon emission computed tomography
SV: Stroke volume
SVR: Systemic vascular resistance
TTT: Total Transit Time
VC: Vena Cava

DESCRIPTION OF DRAWINGS

FIG. 5A-B show maps of area under curve (AUC) and centroid, respectively, for a number of pixels.

FIG. 6A-B show maps of centroid images, wherein the lungs are used as a reference point and a centroid of the mean centroid of vessels in the lungs is used to split the heart model into arterial portion (left) and a venous portion (right).

FIG. 12: a healthy control (normal heart).
FIG. 13: a patient suffering from amyloidosis.
FIG. 14: a patient with leaky valves.
FIG. 17 A-B.

DETAILED DESCRIPTION OF THE INVENTION

Figure 1A:
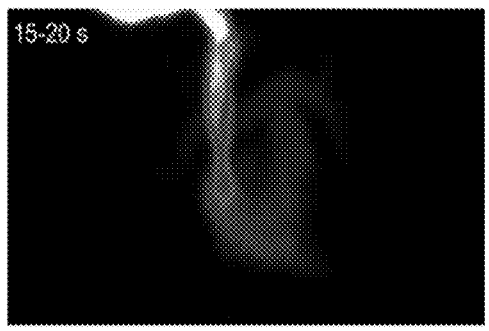
FIG. 1 shows a number of PET tracer concentrations in a heart at various time-points.

The present disclosure relates as mentioned in general to a method for modelling a human heart and/or chambers and cavities therein, such as the left and right atrium, or a human central circulation comprising a human heart, based on PET images. By segmenting the various chambers and large vessels in the central circulation, a segmented model is obtained, from which further parameters and information can be obtained.

Other imaging technologies such as CT, MRI and scintigraphy using gamma-cameras can also be used.

The present disclosure in particular relates to the inventors' finding that, inter aiia, the left atrium (LA) can be segmented automatically using images of bolus area-under-curve and midpoint time. Using the midpoint time of the left-ventricular (LV) cavity as reference, the LA can be segmented as regions with high first-pass activity and a midpoint time shorter than that of the LV. In analogous fashion, the right atrium (RA) can be segmented, and for both the LA and RA an accurate estimate can thereby be obtained of the volume of the specific atrium.

Using this method, data of several patient cohorts were analyzed retrospectively. In 34 patients with documented heart failure (HF) and 14 patients with mitral insufficiency (MI), the LA volume measured by the method of the present invention was compared with that derived from echocardiography or cardiac magnetic resonance imaging (CMR), respectively. 15 patients with suspected cardiomyopathy were scanned twice to assess reproducibility. Finally, the technique was applied to a large group of patients with suspected coronary artery disease, grouped based on their hyperaemic myocardial blood flow (MBF) and coronary flow reserve, to assess LA volumes in progressing coronary artery disease.

A good correlation was found versus echocardiography ($r^2=0.79$) and CMR ($r^2=0.67$) although there were significant differences (p<0.001). Reproducibility of the method was high (intraclass correlation coefficient=0.945). In patients with normal MBF and CFR, the LA index was 26.5±7.0 mL·m$^{-2}$ which increased with progression of cardiac dysfunction (anova p<0.001) and was highest in patients with HF and MI (42.4±17.5 mL·m$^{-2}$ and 59.5±21.5 mL·m$^{-2}$, respectively)

In a first preferred embodiment the present invention thus relates to a method for estimating the volume of an atrium (left (LA) or right (RA)) based on a plurality of emission tomography images, such as positron emission tomography images or single-photon emission computed tomography images, said method comprising the steps of:

a) extracting time activity curves of an injected tracer for a plurality of pixels and/or voxels;

b) isolating first-pass peaks of the time activity curves by
   i. detecting two or more successive frames $t_x$ to $t_{x+n}$ with the maximum downslope wherein x and n are both positive integers;
   ii. extrapolate the maximal downslope using $C_{PET}(t)$ and $C_{PET}(t_{x+n})$ in said successive frames using a fitting procedure, such as for example, but not limited to, exponential fitting, linear fitting or gamma-function fitting;
   iii. defining the first-pass peak as the activity of the original $C_{PET}(t)$ up to $t_{x+n}$ followed by fitting of the downslope starting from the frames with maximal downslope;

c) extracting the centroid-time of said first-pass peak $t_{mid}$ and the area under the curve AUC using the center of mass and total area, respectively, thereby affording a three-dimensional image for both $t_{mid}$ and for AUC, d) defining a ventricle using images showing high ventricle-to-blood contrast, for example but not limited to parametric images generated using basis function methods, or late images of tracer retention, e) defining the ventricular cavity inside of the ventricular region, f) obtaining the cavity time-activity curve, g) extracting the first-pass peak, h) storing the resulting centroid, AUC and location of the ventricular cavity as $t_{mid}$ and AUC as $t_{LV}$, $t_{RV}$, $AUC_{LV}$ and $AUC_{RV}$, i) using $t_{mid}$ and AUC images, defining a mask as all regions with AUC higher than two thirds of $AUC_{LV}$, j) removing from said mask all regions either with
   for LA volume estimation
   iv. $t_{mid}$ less than $t_{LV}$ minus half of the difference between $T_{LV}$ and $t_{RV}$, or
   v. with $t_{mid}$ more than $t_{LV}$ plus the duration of two heartbeats, or
   vi. regions located within the LV cavity,
   vii. defining the center of gravity of the mask,
   viii. removing all regions in said mask more than 1, such as 1.2, 1.3, 1.4, 1.5, 1.6, 1.7, 1.8 or 1.9 times the median distance from this center of gravity, preferably 1.5 times,
   ix. eroding the resulting mask followed by a dilatation/expansion to remove thin tube-like regions i.e. the pulmonary veins,
   for RA volume estimation
   x. $t_{mid}$ more than $t_{LV}$ minus half of the difference between $T_{LV}$ and $t_{RV}$, or
   xi. with $t_{mid}$ more than $t_{RV}$ plus the duration of two heartbeats, or regions located within the RV cavity, or
   xii. regions depicting a vertical tube-like shape i.e. the vena cava, by identifying the vertical slice with a significant, such as 25%, 30%, 35%, 40%, 45%, 50%, 55% or 60%, preferably about 50% increase in area of the mask for the slice as compared to the slice directly above, k) using the total volume of the remaining mask as an estimate of mean LA or RA volume.

In an embodiment parametric images of MBF, PTF (perfusable tissue fraction) and the blood volume corrections $V_A$ and $V_{RV}$ are estimated using a basis function implementation of the single-tissue compartment model for cardiac $^{15}$O-water studies:

$$C_T(t) = PTF \cdot MBF \cdot C_A(t) \otimes e^{-\frac{MBF}{V_T}t} + V_A \cdot C_A(t) + V_{RV} \cdot C_{RV}(t)$$

in which $V_T$ is fixed to 0.91 ml-g$^{-1}$.

Steps a)-k) of the method according to the first preferred embodiment can conveniently be automated by employing a computing device comprising a computer readable storage medium containing instructions that, when executed by a processor, are configured to cause said computing device to execute or perform a method comprising said steps a)-k).

The present disclosure further relates to the inventors' finding that $^{15}$O—H$_2$O-PET can estimate congestion and preload simultaneously and quantitatively by myocardial $^{15}$O—H$_2$O-PET using established transpulmonary dilution methods that resembles those applied by pulse indexed contour cardiac output (PICCO).

The present inventors had hypothesized that end-diastolic volume (GEDV) and lung-water content (EVLW) can be measured by $^{15}$O—H$_2$O-PET examination. Therefore, a study was undertaken to compare EVLW and GEDV measured by PICCO and pulmonary capillary wedge pressure (PCWP) measured by pulmonary arterial catheterization (PAC) with positron emission topographically (PET) derived measures of EVLW and GEDV in a porcine model of pulmonary congestion. The study demonstrated a good correlation between the PET and PICCO measurements of Cardiac Output (CO), EVLW and GEDV, respectively.

In a second preferred embodiment the present invention therefore relates to a method for quantitative estimation of extravascular lung water content (EVLW and global end diastolic volume (GEDV) based on a plurality of emission tomography images, such as positron emission tomography images or single-photon emission computed tomography images, which method comprises the following steps:

a) For the following regions of interest, obtaining the time-activity curves of an injected tracer for a plurality of pixels and/or voxels;
   (1) in vena cava just outside the right ventricle (e.g. pre-right heart, VC);
   (2) at the base of the pulmonary artery (post-right heart/pre-pulmonary, PA);
   (3) one of the pulmonary veins, just outside of the left atrium (pre-left heart, post-pulmonary, PV);
   (4) at the base of the aorta just above the LVOT (post-left heart, AA), b) For each time activity curve, isolating first-pass peaks of the bolus and obtain the corresponding centroid, c) Calculating the following transit times:

Right heart Transit Time (RTT)=PA−VC

Pulmonary Transit Time (PTT)=PV−PA

Left heart Transit Time (LTT)=AA−PV

Total Transit Time (TTT)=AA−VC

Cardiac transit time (CTT)=RTT+LTT.

d) Multiplying each of the above transit times by the tracer (e.g. $^{15}$O—H$_2$O-PET) derived cardiac output (CO) to obtain the volumes of each compartment, Right global end diastolic volume (RGEDV)=CO×RTT pulmonary water volume (PWV)=CO×PTT Left global end diastolic volume (LGEDV)=CO×LTT Intra-thoracic total volume (ITTV)=CO×TTT e) Calculating GEDV as the sum of LGEDV and RGEDV,

GEDV=LGEDV+RGEDV f) Calculating EVLW as the difference between the intrathoracic total volume and intrathoracic blood volume:

EVLW=ITTV−ITBV wherein ITBV is defined as 1.25*GEDV−28.4 mL.

Steps a)-f) of the method according to the second preferred embodiment can conveniently be automated by employing a computing device comprising a computer readable storage medium containing instructions that, when executed by a processor, are configured to cause said computing device to execute or perform a method comprising said steps a)-f).

The general, or overall method for modelling a human heart, and/or chambers and cavities therein, such as the left and right atrium, referred to above is based on a plurality of emission tomography images, such as positron emission tomography (PET) and single-photon emission computed tomography (SPECT) images of said human heart, wherein each image represents concentrations of a tracer that has been injected at a specific time. This general method may comprise a first step of A: extracting time activity curves of a tracer that has been injected for a plurality of pixels and/or voxels. The PET system detects radiation emitted indirectly by the tracer, i.e. after a tracer has been injected in the blood flow, a time activity curve can be obtained by observing the radiation in a pixel/voxel over time. The method may further comprise the step of B: isolating first-pass peaks of the time activity curves, each peak corresponding to an arrival time of the injected tracer at the corresponding pixel/voxel. "First-pass" may refer to the first time the tracer arrives at the pixel/voxel. The tracer will then circulate with lower concentrations.

The method may further comprise the step of C: defining a model comprising at least two portions of the heart, wherein the at least two portions are isolated by selecting pixels and/or voxels based on comparisons of the first-pass peaks against a threshold.

PET is the preferred method for said modelling a human heart and/or chambers and cavities therein, such as the left and right atrium, as referred to above, but other methods for generating tomography images can also be used in the method according to the preferred embodiments of the invention. Some possible options with recommended tracers and/or parameter settings are mentioned below as exemplary embodiments:

Computer tomography, preferably with intravenous injection of iodinated contrast media, using time frames separated by 0.5-10 seconds and a scanning time of 10-120 seconds, preferably 30-60 seconds, CMR, preferably with gadolinium-based contrast media, using time frames separated by 0.1-10 seconds and a scanning time of 10-120 seconds, preferably 30-60 seconds, Single photon emission tomography (SPECT/gamma camera), preferably with radioisotopes (any SPECT-amenable isotope linked with any molecule, as long as said isotope-molecule ligand is not retained in lung tissue during the first pass through the lungs after injection, using time frames separated by 3-10 seconds and a scanning time of 10-120 seconds, preferably 30-60 seconds, or PET with any PET-amenable radioisotope, as long as said isotope and the labeled molecule is not retained in lung tissue during the first pass through the lungs after injection, using time frames separated by 1-10 seconds and a scanning time of 10-120 seconds, preferably 30-60 seconds.

The method according to the preferred embodiments described hereinabove may involve various techniques for defining contours and regions for the portions of interest. The concentration of tracer, or for example the magnitude of the peaks, will be relatively high in the chambers and large vessels of the heart in relation to surrounding tissue. By calculating the area under the curve (AUC) and the x-coordinate of the center of mass (centroid time) for a number of pixels, images of AUC and of centroids are obtained. The general method may further comprise the step of D arranging the at least two portions in relation to each other by comparing the arrival times of the first-pass peaks of the pixels and/or voxels in the portions, thereby obtaining a segmented model of the human heart. By making use of a known sequential order of the portions, the portions can be arranged in relation to each other in order to obtain the segmented model. If steps C and D of the general method are then iteratively repeated by dividing the at least two portions further into sub-portions (step C of the general method) and arranging the sub-portions in relation to each other by comparing the arrival times of their first-pass peaks (step D of the general method), the model of the human heart may be further segmented. For example, a segmented model comprising chambers and large vessels of the heart may be obtained, such as a model comprising the vena cava, the right atrium, the right ventricle, the base of the pulmonary artery, the pulmonary veins close to the left atrium, the left atrium, the left ventricle and the base of the ascending aorta of the heart.

The emission tomography images may be positron emission tomography images or single-photon emission computed tomography images. A radiotracer can be said to be a type of radioligand that is used for emission tomography imaging. There are a number of radiotracers that can be used in PET, the radiotracers comprising radio-isotopes such as C-11, N-13, O-15, and F-18. PET is increasingly used to quantify the blood flow in the heart muscle itself, one of the most important prognostic and diagnostic markers in heart disease. The PET tracer $^{15}$O-water is the most accurate way of obtaining blood flow. In one embodiment of the presently disclosed method, the tracer is $^{15}$O-water.

Before the presently disclosed method is performed, a tracer must have been injected in the blood flow, preferably in a vein entering the right atrium of the heart, such as just before the vena cava. In one embodiment, the method comprises the step of injecting a tracer in a vein entering the heart.

Isolation of Portions

Figure 1B:
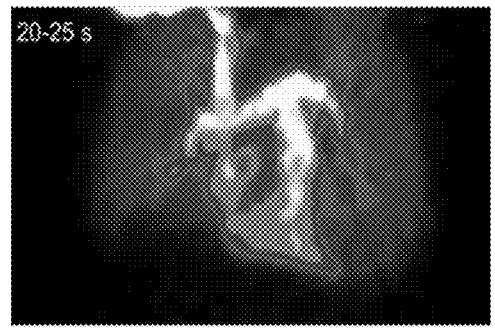
Figure 1C:
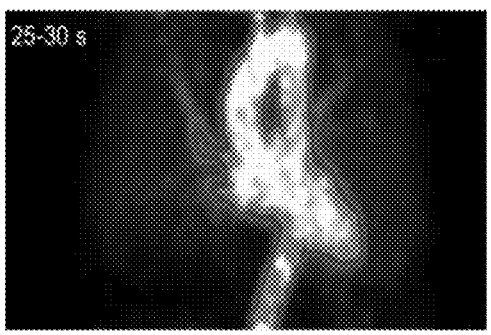
Figure 1D:
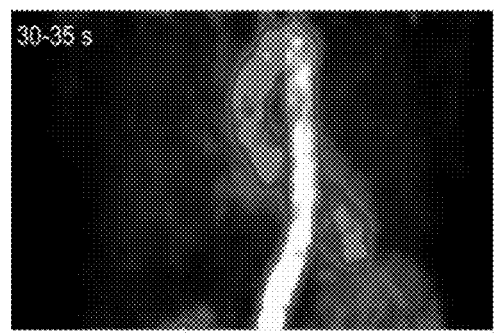

During PET, an injected tracer can be imaged by a PET scanner as it propagates through the body, and in particular through the blood vessels. The PET scanner may thereby generate a number of sequential images of tracer concentrations at a number of points in time. The points may represent images during for example a time range of 30 seconds, 1 minute, 2 minutes or longer and may be split in intervals (and thereby images) of for example every second, 5 seconds, 10 seconds. When starting the PET acquisition simultaneous with tracer injection, the bolus of the PET tracer can be tracked. In the present disclosure, bolus may be referred to as a high concentration of the PET tracer in a small injected volume, defining a concentration area or region. In particular during a limited time after injection, a bolus may be tracked. After some time, the tracer is distributed throughout the entire body and there is no bolus in the meaning of the present disclosure. An example of the propagation of the tracer (and bolus) can be seen in FIGS. 1A-D. It can be seen that the bolus arrives in the vena cava (VC) (FIG. 1A), then further on to the pulmonary arteries (FIG. 1B), then further on to the pulmonary veins, left side of the heart and the aorta (FIG. 1C) and then further on to the descending aorta (FIG. 1D).

The tracer then distributes throughout the body. Typically, in the known systems and methods, these following images are then used to calculate physical progress, such as perfusion. In the present disclosure, the initial sequence of images following an injection are used to model a segmented model of the human heart.

Figure 2:
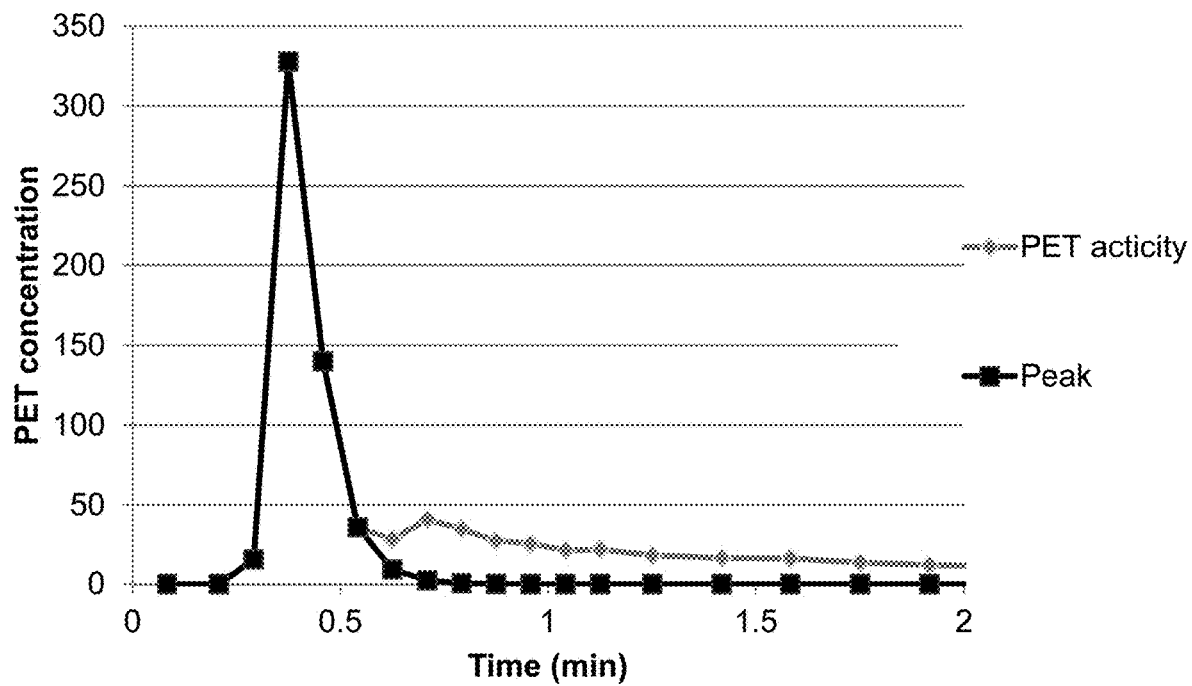
FIG. 2 shows a PET tracer concentration over time for one pixel and a corresponding exponential downslope fitting of the peak.

In one step an indicator-dilution analysis may be performed in order to extract a time activity curve for a pixel/voxel of the tracer. An example of a PET concentration curve for a pixel/voxel is shown in FIG. 2. The process is performed for a number of pixels/voxels. A pixel or voxel may comprise a blood fraction. A pixel comprising a large blood fraction will typically have a distinct peak as shown in FIG. 2. It can be seen in FIG. 2 that the concentration is very low immediately after the tracer has been injected. When the bolus arrives in the blood represented by the pixel, there is a rapid increase of concentration and a peak. After the bolus has passed the pixel, the concentration goes back to a more constant and lower level.

Preferably the peaks, which may be first-pass peaks, are identified and preferably isolated in another step, which can be achieved by means of exponential downslope fitting. After correction for recirculation of tracer, a peak curve is obtained, which is also shown in FIG. 2. From the peak, the area under the curve may be calculated and a centroid time may also be calculated, which corresponds to the center of mass of the x-axis of the diagram of FIG. 2. These values may then be represented as a map for a number of pixels/voxels as shown in FIGS. 5A-B. FIG. 5A shows the AUC values for a number of pixels, and FIG. 5B shows a map of the centroid of the bolus. In FIG. 5A the cavities of the heart and the descending aorta are visible in the map. The lungs show some activity and the rest of the body shows no peak.

FIG. 5B shows a map of the centroid of the bolus. The figure may thus be seen as a representation of arrival times of the bolus. It can be seen that there is a region with minimal centroid, which corresponds to the right atrium, corresponding to a dark area using the color scale. A slightly higher arrival time, i.e. the region with slightly brighter color, represents the right ventricle of the heart. The arrival times (or centroids) for the region corresponding to the lungs are slightly higher (i.e. later in time, brighter) than that of the right side of the heart, but lower (darker) than the left side of the heart. Finally, the left atrium, left ventricle and descending aorta show (in that order) increasing centroids (increasingly lighter grey) that are each higher than that of the lungs.

As explained below, according to the present invention the two types of information in the maps (physical placement of bolus and timing of bolus) may be combined in order to isolate and arrange the chambers and large vessels in the central circulation, thereby obtaining segmented model of the human heart, including specifically an estimate of the volume of the left or right atrium of said human heart.

The step of defining a model may comprise at least two portions of the heart comprises the step of isolating the two portions from surrounding tissue. In one embodiment of the presently disclosed method the at least two portions are isolated by selecting pixels and/or voxels based on comparisons of the areas of the peaks against a threshold. This may correspond to an isolation of a physical region by making use of the assumption that the bolus stays in the blood, i.e. the vessels, in this initial phase, and that the images therefore are assumed to reflect the displacement of blood in the circulation. In one embodiment the at least two portions are isolated by selecting pixels and/or voxels based on comparisons of the areas of the peaks against a threshold. A certain minimum level of the peaks is considered to correspond to a pixel that is within a blood vessel whereas the pixels that are below the threshold are considered to represent other tissue.

As stated above the tracer that has been injected may be a bolus of radio-opaque contrast media, wherein the first-pass peak of each time activity curves corresponds to the bolus arriving at the pixel/voxel. In one embodiment, a center of mass in time is obtained for each of the time activity curves of the pixels/voxels. This information may then be combined to obtain a segmented model of the human heart according to the present disclosure, including in particular an estimate of the volume of the left or right atrium of said human heart.

Segmentation

One purpose of the invention is to segment the various chambers and large vessels in the central circulation (such as the heart, the lungs and the pulmonary vessels). In one embodiment, the segmentation is initially performed such that a first portion of said two portions is a left portion of the heart and the second portion of said two portions is a right portion of the heart. From the isolation of portions, as explained and showed in for example FIG. 5A, a number of portions are available. As shown in FIG. 5B, there is also timing information available for the portions. Now, by arranging the at least two portions in relation to each other by comparing the arrival times of the first-pass peaks of the pixels and/or voxels in the portions, a segmented model of the human heart is obtained which in a specific embodiment can be employed to obtain an estimate of the volume of the left or right atrium of said human heart. More specifically, when the centroid and blood volume (scaled AUC) images have been obtained, they can be processed them using some landmark information. If for example the lungs are identified, manually or automatically, the remaining regions of the central circulation can be split into an arterial (centroid >lung) and a venous (centroid <lung) region.

In one embodiment the plurality of pixels and/or voxels correspond to reference points in the human heart. Each reference point may correspond to a chamber or vessel of the heart. By assigning a reference point to each portion, the arrival times of the reference points can be compared to determine how the portions are to be arranged. If the steps of c) defining a model comprising at least two portions of the heart, wherein the at least two portions are isolated by selecting pixels and/or voxels based on comparisons of the first-pass peaks against a threshold and d) arranging the at least two portions in relation to each other by comparing the arrival times of the first-pass peaks of the pixels and/or voxels in the portions, are iteratively repeated the model may be further segmented. By dividing one or more of the at least two portions further into sub-portions and arranging the sub-portions in relation to each other by comparing the arrival times of their first-pass peaks, a model of the chambers and large vessels in the central circulation may be obtained.

In one embodiment the chambers to be modeled are selected from the right atrium, the right ventricle, the left atrium and the left ventricle of the heart. More preferably the at least two portions correspond to chambers and large vessels of the heart selected from the vena cava, the right atrium, the right ventricle, the base of the pulmonary artery, the pulmonary veins close to the left atrium, the left atrium, the left ventricle and the base of the ascending aorta of the heart. In one embodiment the steps of c) defining a model comprising at least two portions of the heart, wherein the at least two portions are isolated by selecting pixels and/or voxels based on comparisons of the first-pass peaks against a threshold and d) arranging the at least two portions in relation to each other by comparing the arrival times of the first-pass peaks of the pixels and/or voxels in the portions, are iteratively repeated until the vena cava, the right atrium, the right ventricle, the base of the pulmonary artery, the pulmonary veins close to the left atrium, the left atrium, the left ventricle and the base of the ascending aorta of the heart have been obtained. The at least two portions, corresponding to chambers and large vessels of the heart, may form a sequential flow model. By using a sequential flow model, such as a flow model comprising any of the vena cava, the right atrium, the right ventricle, the base of the pulmonary artery, the pulmonary veins close to the left atrium, the left atrium, the left ventricle and the base of the ascending aorta of the heart in the order blood flows through them, the arrival times for the reference points can be compared and arranged in order to identify the segments.

As stated, by comparing the arrival times of the first-pass peaks of the pixels and/or voxels in the portions, the portions can be arranged in the image taking into account a predetermined order of the portions, thereby obtaining a segmented model of the human central circulation. By assigning reference points to the portions, transit times can then be calculated between any two reference points of the portions and/or sub-portions is calculated. The transit times between different portions and the segmented model of the heart made then be used to further extract and calculate a number of parameters from the scan, which would otherwise require additional clinical examination.

In one embodiment the transit time is calculated between a reference point at an entering boundary of the right portion of the heart and a reference point at an exiting boundary of the right portion of the heart, and/or between a reference point at an entering boundary of the lungs and a reference point at an exiting boundary of the lungs, and/or between a reference point at an entering boundary of the left portion of the heart and a reference point at an exiting boundary of the left portion of the heart. Transit times may also be calculated between any two or more sub-portions.

Applications

The segmented model may be used for a number of applications. In one embodiment the method further comprises an additional step of calculating volumes of the portions and/or sub-portions based on the segmented model. A cardiac output may also be calculated based on the obtained segmented model. Transit times between the portions may be multiplied by the cardiac output to calculate the effective volume of each cardiac chamber. Therefore, in a further embodiment the step of calculating volumes of the portions and/or sub-portions comprises the step of multiplying a transit time for a portion or sub-portion with a calculated cardiac output for the same portion/sub-portion. Dilated cardiac chambers are a sign of cardiac disease and the specific chamber dilated is indicative of the type of cardiac disease. In addition, the global end-diastolic volume can be calculated non-invasively using this method. The volume is a strong marker of cardiac pre-loading conditions but would normally require arterial catheterization and is therefore only used in the critically ill patients.

The first preferred embodiment of the present invention relates to an example in the cardiac disease area. The left atrial (LA) volume is a marker of cardiovascular risk independent of myocardial blood flow (MBF), and assessing both simultaneously aids in risk stratification. However, deriving LA volume from PET data is labour intensive and prone to observer variation.

Quantitative myocardial blood flow (MBF) measurements using Positron Emission Tomography (PET) are increasingly being used to assess ischemic burden in coronary artery disease (CAD) or to assess microvascular dysfunction (MVD). Both CAD and MVD can lead to reduced cardiac function and heart failure. As a consequence, structural and functional information is required on top of MBF measurements to fully evaluate the disease severity. Assessment of left-ventricular (LV) structure and function can be performed simultaneously with quantitative MBF measurements, yielding information on systolic function. Left-atrial (LA) structure, on the other hand, is more complex to assess and often requires separate structural imaging yet it provides a powerful marker of LV filling pressures and, consequently, diastolic function.

The prognostic relevance of LA volumes has been demonstrated in several studies [Tsang T S M et al. J Am Coll Cardiol. 2006; 47:1018-23], [Moller J E et al. L Circulation 2003; 107:2207-12] and [Benjamin E J, et al. Circulation 1995; 92:835-41], and it was found to be a risk factor in cardiac events independent of MBF or coronary flow reserve (CFR). During the first-pass of a bolus of a PET tracer through the heart and lungs, only the blood pool is visible. Therefore, this phase can be utilized to delineate the left-atrium by manually tracing the left-atrial contours as shown before [Koh A S et al. Eur J Nucl Med Mollmaging. 2015; 42:1551-61]; however this is labor intensive and prone to observer variability.

Hitherto a fully automated analysis of the first-pass phase of dynamic cardiac PET scans to obtain the left atrial volume in addition to MBF and CFR has not been available, therefore the first preferred embodiment of the present invention, which relates to an automated method for obtaining LA volume from dynamic MBF PET scans, is a clinically highly significant development.

Said automated method, which is discussed further in the following, was validated by a comparison with either echocardiography or cardiac magnetic resonance (CMR) imaging. The reproducibility of the method was assessed in a test-retest setting including testing using a different tracer. Finally, the new method was applied to a large cohort of patients referred for standard clinical assessment of MBF.

PET-CT for Estimation of Atrium Volume

Subjects were instructed to fast >4 hours prior to each PET study, except for water and medicine prescribed for daily intake. After a scout CT scan, a low-dose CT scan (120 kV, 30 mAs, 4 mm slice thickness) was performed. Following this, a 6-min list mode emission scan was performed, starting simultaneously with a bolus injection of 400 MBq of $^{15}$O-water as a 5-10 mL bolus (1 mL·s$^{-1}$) in a peripheral vein, using an automatic injection system, followed by a 35 mL saline flush (2.0 mL·s$^{-1}$) similarly as described in pending PCT application WO 2016/203055. Emission data were acquired in list-mode and reconstructed in a dynamic series with 22 time frames (1×10 s, 8×5 s, 4×20 s, 2×15 s, 3×20 s, 2×30 s, 2×60 s) for $^{15}$O-water.

All dynamic images were reconstructed using the standard dynamic reconstruction protocols of each scanner, applying all routine corrections for attenuation, scatter, dead-time and decay as supplied by the vendor. Except for MR patients, all subjects underwent an adenosine-induced stress scan after continuous infusion of 140 ug/kg. In case of repeat studies, the second $^{15}$O-water scan was started at least 10 minutes (5 half-lives) after the end of the first $^{15}$O-water scan.

Echocardiography

Echocardiogaphic recordings were obtained using a Vivid 9 scanner (version BT12, GE Vingmed, Ultrasound, Horten, Norway). LA volumes were determined using the biplane method as for LV ejection fraction, but using the "Volume/ atria" function in EchoPAC (GE Vingmed, Ultrasound, Horten, Norway). Briefly, the endocardial border of the LA was traced in end-systole, just before the opening of the mitral valve, and in end-diastole at closing of the mitral plane in both apical four- (4CH) and two-chamber (2CH) views (see FIG. 15). The atrial appendage and the pulmonary veins were excluded. During image acquisition, care was taken to avoid deviation in LA length (LAL) of more than 0.5 cm between 4CH and 2CH. An average of 3 cardiac cycles were measured, but in case of atrial fibrillation, 5 cycles was used.

Calculation of Left Atrial Volume

Left atrial volume was obtained by tracking the arrival time and location of the first-pass bolus. This requires creation of images of both the bolus arrival time and area under the curve and comparison of these parameters with reference values of the right- and left-ventricular cavity.

Parametric Images of Bolus Area and Arrival Time

Data were analyzed [see Harms H J et al. Automatic generation of absolute myocardial blood flow images using $^{15}$O—H$_2$O and a clinical PET/CT scanner. Eur J Nucl Med Mollmaging. 2011; 38:930-9 and Harms H J et al. Automatic Extraction of Myocardial Mass and Volume Using Parametric Images from Dynamic Nongated PET. J Nucl Med [Internet] 2016; 57:1382-7] as follows: First, for each voxel the first-pass peak was extracted automatically. For this, the two successive frames $t_1$ and $t_2$ with the maximum downslope were detected first. $C_{PET}(t_1)$ and $C_{PET}(t_2)$ in these frames was then used to define an exponential fit of the downslope after which the first-pass peak was then defined as the activity of the original $C_{PET}(t)$ up to $t_2$ followed by the exponential fit of the downslope starting from the frames with maximal downslope. The centroid-time of this peak $t_{mid}$ and the area under the curve AUC were extracted using the center of mass and total area, respectively. This results in a three-dimensional image for both $t_{mid}$ (FIG. 11A) and for AUC (FIG. 11B). Regions with high AUC and $t_{mid}$ less than 1.5 minute were identified and considered the blood region.

Segmentation of the Left and Right Ventricle

Arterial and venous input functions were obtained using cluster analysis [Harms H J, et al. Eur J Nucl Med Mollmaging. 2011; 38:930-9] using 6 clusters. After this, parametric images of MBF, PTF and the blood volume corrections $V_A$ and $V_{RV}$ were estimated using a basis function implementation of the single-tissue compartment model for cardiac $^{15}$O-water studies:

$$C_T(t) = PTF \cdot MBF \cdot C_A(t) \otimes e^{-\frac{MBF}{V_T}t} + V_A \cdot C_A(t) + V_{RV} \cdot C_{RV}(t)$$

in which $V_T$ was fixed to 0.91 ml·g$^{-1}$.

Resulting parametric images were automatically reoriented to short-axis images and the left-ventricle was segmented using the methods described previously [Harms H J et al. J Nucl Med [Internet] 2016; 57:1382-7]. Using the same set of short-axis images, the right-ventricle (RV) was segmented in a similar way as the LV, except that $V_{RV}$ instead of $V_A$ images were used as starting point for the circumferential profiling.

LV and RV cavities were then defined as all regions inside of the myocardial regions at least 1.3 cm (twice an assumed PET resolution of 6.5 mm full-width at half maximum) away from segmented myocardial regions. For both cavities, the time-activity curve was obtained, the first-pass peak was extracted and resulting values for $t_{mid}$ and AUC were stored as $t_L$, $t_{RV}$, AUC$_{LV}$ and AUC$_{RV}$.

Segmentaton of the left Atrium

Using parametric $t_{mid}$ and AUC images, a mask was defined as all regions with AUC high than $\frac{2}{3}^{rd}$ of AUC$_{LV}$. Then, all regions either with $t_{mid}$ less than $t_{LV}$ minus half of the difference between $t_L$ and $T_{RV}$, with $t_{mid}$ more than $t_{LV}$ plus the duration of two heartbeats, or regions located within the LV cavity were removed from the mask, assuming that the mitral plane was correctly defined during segmentation of the LV wall.

To separate the aorta from the left-atrium, the left-ventricular outflow tract was defined using the most basal short-axis plane of the myocardial segments. In this plane, the LVOT was defined as the regions with a wall thickness of 0 and was extrapolated to the more basal planes until two separate regions were found.

In order to remove the pulmonary veins from the mask, first the center of gravity of the mask was defined. All regions in the mask more than 1.5 times the median distance from this center of gravity were removed, assuming at least a moderate degree of sphericity in the left atrium. Finally, the resulting mask was eroded followed by a dilatation to remove thin tube-like regions i.e. the pulmonary veins. The total volume of the remaining mask was obtained and used as estimate of mean LA volume.

Data Analysis

Patients in group 5 were divided based on their respective stress MBF values. Patients with stress MBF above 2.3 mL/g/min and coronary flow reserve above 2.5 in all segments were classified as normals, patients with stress MBF below 2.3 mL/g/min in a single region were classified as 1V, patients with global CFR below 2.5 but above 1.5 were considered 3V and patients with CFR below 1.5 were classified as MVD.

Correlation and agreement between PET and echo measures were assessed using linear regression and Bland Altman plots and intra-class correlation coefficients (ICC) were used to assess reproducibility. A paired t-test was used to assess the presence of systematic differences. Repeatability coefficient (RPC) was defined as 2 times the standard deviation of the difference. Differences between patient groups were assessed using student's t-tests. Data are presented as mean±SD.

For CMR and echocardiography, a weighted mean LA volume was calculated as LA$_{mean}$=(LA$_{ESV}$+2*LA$_{EDV}$)/3.

Results

Segmentation of the left atrium was successful in all subjects. Correlation of PET-derived LA volume and echocardiographically-derived LA volume for HF patients (FIG. 7) and CMR-derived LA volumes for MR patients (FIGS. 8 and 9) was high (r=0.88 and r=0.82, respectively). Reproducibility of the method (FIG. 10) was excellent (ICC=0.93) and a reproducibility coefficient of 8.6 mL/m$^2$.

Discussion, Atrium Estimation

The invention disclosed herein presents in a first preferred embodiment an automated method of segmenting the left or right atrium in dynamic $^{15}$O-water PET studies, yielding atrium volume information in addition to standard information MBF. A high correlation was found with anatomical gold-standard measures and the method was highly reproducible in a test-retest setting.

The MI patients included in this study underwent paired $^{15}$O-water and $^{11}$C-acetate studies and an excellent correlation was found between $^{15}$O-water and $^{11}$C-acetate derived LA volumes or between $^{11}$C-acetate and CMR. In addition, a good inter-tracer reproducibility was found in a cohort of patients that underwent paired $^{15}$O-water and $^{82}$Rb studies, provided that only $^{82}$Rb studies with a relatively rapid infusion were included. While further validations are required with different tracers and the appropriate gold standard, these results indicate that the method as disclosed herein can be applied successfully to a variety of tracers.

The method disclosed hereinabove according to the second preferred embodiment, relates to an automated method for quantitative estimation of extravascular lung water content (EVLW) and global end diastolic volume (GEDV) to be discussed further in the following, was validated by a comparison of EVLW and GEDV measured by PICCO and pulmonary capillary wedge pressure (PCWP) measured by pulmonary arterial catheterization (PAC) with positron emission topographically (PET) derived measures of EVLW and GEDV in a porcine model of pulmonary congestion.

Data were analyzed using in-house developed software. A set of 4 regions of interest (ROIs) were drawn: (1) in vena cava just outside the right ventricle (e.g. pre-right heart, VC); (2) At the base of the pulmonary artery (post-right heart/pre-pulmonary, PA); (3) One of the pulmonary veins, just outside of the left atrium (pre-left heart, post-pulmonary, PV); (4) At the base of the aorta just above the LVOT (post-left heart, AA). For each ROI the time-activity curves were obtained and the peak of the first-pass of the bolus was isolated, obtaining the corresponding centroid for each curve.

Subsequently the following transit times can be calculated:

Right heart transit time (RTT)=PA−VC

Pulmonary Transit Time (PTT)=PV−PA

Left heart Transit Time (LTT)=AA−PV

Total Transit Time (TTT)=AA−VC cardiac transit time (CTT)=RTT+LTT.

Each of these factors were then multiplied with the $^{15}$O—H$_2$O-PET derived cardiac output (CO) to get the volumes of each compartment:

Right global end diastolic volume (RGEDV)=CO× RTT pulmonary water volume (PWV)=CO×PTT Left global end diastolic volume (LGEDV)=CO× LTT Intra-thoracic total volume (ITTV)=CO×TTT Finally, GEDV is defined as the sum of LGEDV and RGEDV. It is important to acknowledge that PICCO measures the entire volume from the injection site of the cold saline to the arterial termistor site excluding only lung water volume whilst the PET method represents solely the intra-cardiac volume. Hence, it was anticipated that the PET derived GEDV was lower than GEDV obtained from PICCO.

To calculate intrathoracic blood volume (ITBV) a relation was applied between a purely intravascular agent and an agent that dilutes in entire water content: (ITBV= 1.25*GEDV−28.4 mL). Hereafter, the EVLW is defined as the difference between the intrathoracic total volume and intrathoracic blood volume: EVLW=ITTV−ITBV.

Forward stroke volume (SV) was measured by dividing cardiac output by heart rate.

Results

Cardiac Output (CO) measured by PICCO and PET correlated ($r^2$=0.79, p<0.001). Despite the initial changes in HR and invasive hemodynamics, CO was unaffected (PICCO: p=0.80, PET: p=0.83) until saline was initiated. However, CO did not differ between 3 L and 10 L of saline (PICCO: p=0.80, PET: p=0.39) and there was no difference between PICCO and PET measurements of CO (p=0.85, two way anova, test for interaction). These changes demonstrated an overall decrease in stroke volume (SV) throughout the study (PICCO: p=0.004, PET: p=0.03). However, this was predominantly driven by an initial decrease in SV from baseline (BL) to AB (PICCO: p=0.001, PET: p=0.03), and then followed by an increase after initiation of saline infusion (p<0.001 for both PICCO and PET) (table 1).

TABLE 1

Changes in invasive and PET parameters

| | BASELINE | AB | AB-3L | AB-10L | ANOVA P-VALUE |
|---|---|---|---|---|---|
| Arterial and pulmonary hemodynamic parameters | | | | | |
| HR (bpm) | 87 ± 13 | 108 ± 15 | 119 ± 19 | 121 ± 13 | <0.001 |
| CVP (mmHq) | 6 ± 1 | 10 ± 1 | 16 ± 1 | 19 ± 2 | <0.001 |
| mPAP (mmHg) | 17 ± 4 | 33 ± 3 | 37 ± 4 | 42 ± 7 | <0.001 |
| PCWP (mmHq) | 8 ± 2 | 16 ± 3 | 27 ± 6 | 29 ± 5 | <0.001 |
| TPG (mmHq) | 9 ± 3 | 16 ± 3 | 11 ± 5 | 12 ± 3 | 0.002 |
| MAP (mmHg) | 100 ± 16 | 154 ± 15 | 140 ± 13 | 131 ± 9 | <0.001 |
| PICCO parameters | | | | | |
| CO (L/min) | 7.6 ± 1.6 | 7.4 ± 0.8 | 10.0 ± 1.8 | 10.2 ± 1.7 | <0.001 |
| SV (ml) | 88 ± 18 | 70 ± 12 | 86 ± 20 | 85 ± 16 | 0.004 |
| GEDV (ml) | 1068 ± 170 | 1133 ± 122 | 1263 ± 101 | 1254 ± 85 | <0.001 |
| EVLW (ml) | 521 ± 76 | 543 ± 51 | 673 ± 108 | 929 ± 325 | <0.001 |

TABLE 1-continued

Changes in invasive and PET parameters

| | BASELINE | AB | AB-3L | AB-10L | ANOVA P-VALUE |
|---|---|---|---|---|---|
| PET parameters | | | | | |
| CO (L/min) | 7.5 ± 2.3 | 7.6 ± 1 | 9.2 ± 1.7 | 10 ± 1.3 | 0.005 |
| SV (ml) | 85 ± 20 | 72 ± 12 | 78 ± 15 | 83 ± 8 | 0.03 |
| GEDV (ml) | 364 ± 60 | 433 ± 67 | 452 ± 51 | 524 ± 92 | <0.001 |
| EVLW (ml) | 566 ± 151 | 630 ± 143 | 730 ± 193 | 797 ± 231 | 0.001 |
| MBF (ml/min/gram) | 1.23 ± 0.38 | 1.69 ± 0.25 | 2.21 ± 0.38 | 2.54 ± 0.58 | <0.001 |
| CT parameters | | | | | |
| HU | −707 ± 48− | −687 ± 47 | −635 ± 32 | −607 ± 26 | <0.001 |

Figure 18:
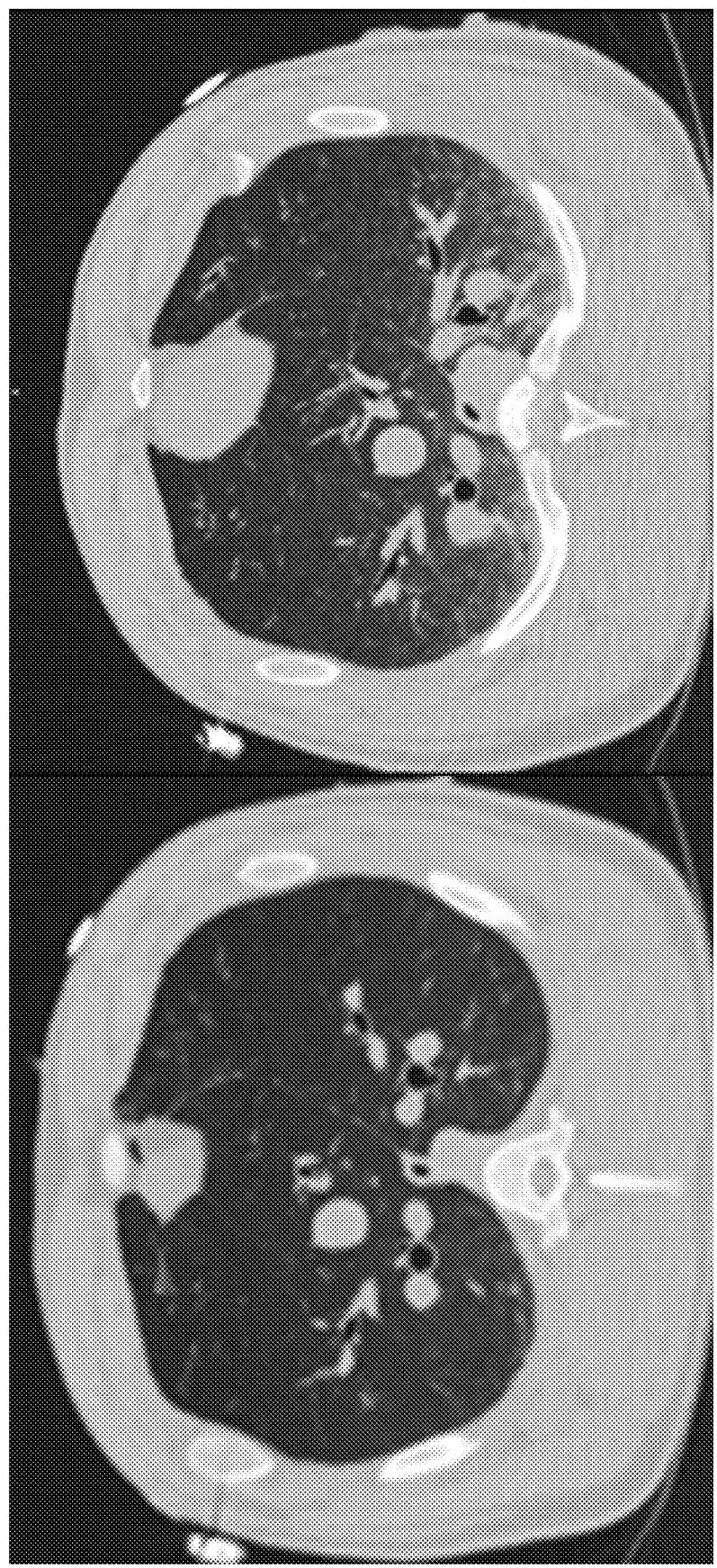
FIG. 18 Coronal CT scan of a pig at baseline (left) and the end of study (right), demonstrating the congestion evident by increased lung density (white areas).

EVLW measured by PICCO and PET correlated ($r^2$=0.41, <0.001), and increased throughout the study (table 1). Houndfield unit (HU) increased gradually during the study and correlated positively with EVLW measured by either PICCO or PET (p<0.001, for both), and congestion was demonstrated (FIG. 18). However, HU had the best correlation with EVLW measured by PET (PICCO: $r^2$=0.36, PET: $r^2$=0.45 (p<0.001 for both)).

Similar to EVLW, GEDV measured by PICCO and PET correlated (FIG. 17, $r^2$=0.41 (p<0.001)) and increased steadily from BL to AB-10L (p<0.001, table 1) despite the initial decrease in stroke volume (SV).

The present results demonstrate that a single dynamic $^{15}$O—H$_2$O PET examination can be applied to measure EVLW and GEDV, and hence, quantitatively assess the degree of pulmonary congestion and preload. Such findings are highly interesting and clinically relevant, as the method according to the second preferred embodiment now presents a way to non-invasively perform these measures in outpatient settings during normal daily practice and evaluate them in the context of prognosis and therapeutical approaches.

Hence, additional prognostic value can be derived from $^{15}$O—H$_2$O-PET examinations. The results demonstrate that a single dynamic $^{15}$O—H$_2$O-PET examination can be applied to measure extravascular lung water content (EVLW) and global end-diastolic volume (GEDV), and hence, quantitatively assess the degree of pulmonary congestion and preload. Importantly, these parameters are spin-off during myocardial perfusion imaging and do not presuppose additional PET examinations. The method thus provides a convenient and practical way to non-invasively perform these measures in outpatient settings during normal daily practice, and evaluate them in the context of prognosis and therapeutical approaches.

The methods presented according to the first and second preferred embodiments are fully automated, making use of the displacement of the bolus during the first-pass through the heart. This phase is to a large extent tracer independent, and in other, separate embodiments of the invention the methods as disclosed herein can be translated to any PET tracer.

The present disclosure further relates to a method for identifying a cardiac disease by analyzing the volumes of the sub-portions of the segmented model obtained in the method for modelling a human heart according to any of preceding claims.

System

The present disclosure further relates to a system for modelling a human heart based on a plurality of emission tomography images, such as positron emission tomography images or single-photon emission computed tomography images, of said human heart, said system being arranged to perform the method for modelling a human heart according to method as described in the present disclosure. This means that preferably the system comprises an emission imaging device arranged to provide the emission tomography images; and a processor or other means arranged to perform the method for modelling a human heart.

Furthermore, a non-transitive, computer-readable storage device for storing instructions that, when executed by a processor, performs the various methods described hereinabove according to the present disclosure. The methods may be implemented as software that is readable and executable by for example a computer processor.

DETAILED DESCRIPTION OF THE DRAWINGS

The invention will in the following be described in greater detail with reference to the accompanying drawings. The drawings are exemplary and are intended to illustrate some of the features of the presently disclosed method and system for modelling a human heart and/or chambers and cavities therein, such as the left and right atrium, and are not to be construed as limiting to the presently disclosed invention.

FIG. 1 shows a number of PET tracer concentrations in a heart at various time-points after an injection of the tracer in the blood flow before entering the heart. In FIG. 1A it can be seen that the bolus has arrived in the vena cava. In FIG. 1B the bolus is located in the right side of the heart and the pulmonary arteries. In FIG. 1C the bolus has arrived in the pulmonary veins, left side of the heart and the aorta. In FIG. 1D the bolus is located in the descending aorta. After this phase, the tracer distributes throughout the body and the bolus is lost in the sense that there is no well-defined bolus.

FIG. 2 shows a tracer concentration over time for one pixel and a corresponding exponential downslope fitting of the peak. The concentration is initially low and increases rapidly when the bolus passes the pixel. After the bolus has passed the pixel, the concentration goes back to a more constant and low level. It can be noted that the tracer concentration curve is hidden behind (and consequently substantially follows) the peak curve for the first 0.6 min.

Figure 3:
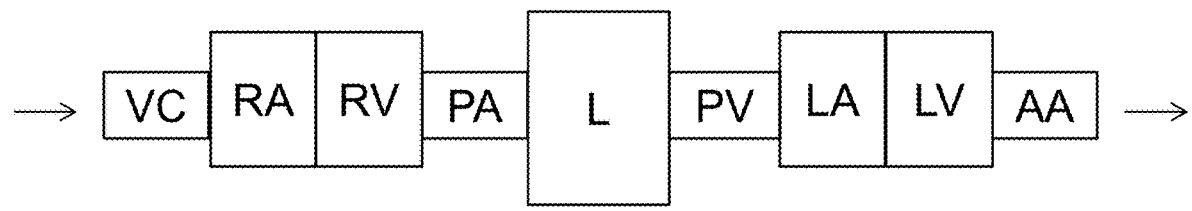
FIG. 3 shows a sequential block diagram of various chambers and large vessels in the central circulation.

FIG. 3 shows a sequential block diagram of various chambers and large vessels in the central circulation. The sequence represents the Vena Cava (VC), Right Atrium (RA), Right Ventricle (RV), the Pulmonary Artery (PA), the Lungs (L), the Pulmonary Veins (PV), the Left Atrium (LA), the Left Ventricle (LV) and the Ascending Aorta (AA).

Figure 4:
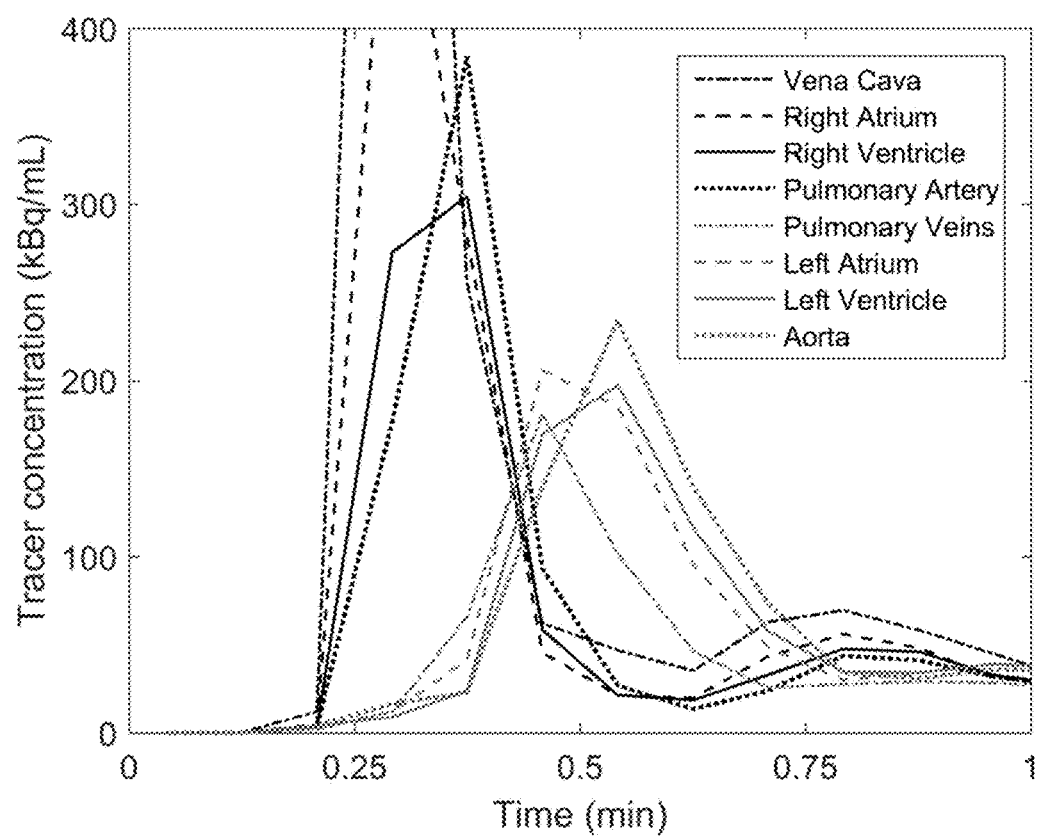
FIG. 4 shows PET tracer concentrations for a number of pixels located in different portions of a heart.

FIG. 4 shows PET tracer concentrations for a number of pixels located in different portions of a heart. The portions, and as a consequence also the different for which the tracer concentrations are shown over time, are: Vena Cava (VC), Right Atrium (RA), Right Ventricle (RV), the Pulmonary Artery (PA), the Pulmonary Veins (PV), the Left Atrium (LA), the Left Ventricle (LV) and the Ascending Aorta (AA). The curves show a gradual shift in the arrival time of the injected bolus of PET radiotracer in each of the successive regions. It can be noted that there is a small gap in time between the pulmonary artery and the pulmonary veins, which is explained by the time that bolus passes the lungs.

FIG. 5A-B show maps of area under curve (AUC) and centroid, respectively, for a number of pixels. The map of 5A can be said to represent a strength of the bolus at different locations. FIG. 5A shows the AUC values for a number of pixels, and FIG. 5B shows a map of the centroid of the bolus. In FIG. 5A the cavities of the heart and the descending aorta are visible in the map. The lungs show some activity and the rest of the body shows no peak. FIG. 5B can be said to show a representation of arrival times of the bolus. There is a region with minimal centroid, which corresponds to the right atrium, corresponding to a dark area using the color scale. A slightly higher arrival time, i.e. the region with slightly brighter color, represents the right ventricle of the heart. The arrival times (or centroids) for the region corresponding to the lungs are slightly higher (i.e. later in time, brighter) than that of the right side of the heart, but lower (darker) than the left side of the heart. Finally, the left atrium, left ventricle and descending aorta show (in that order) increasing centroids (increasingly bright color) that are each higher than that of the lungs.

FIG. 6A-B show maps of centroid images, wherein the lungs are used as a reference point and a centroid of the mean centroid of vessels in the lungs is used to split the heart model into arterial portion (left) and a venous portion (right). If the lungs have been segmented and the location of the lungs is considered known, the mean centroids of the mid-size vessels in the lungs can be used to split the blood regions into an arterial (centroid >lung) and venous (centroid <lung) region.

Figure 7:
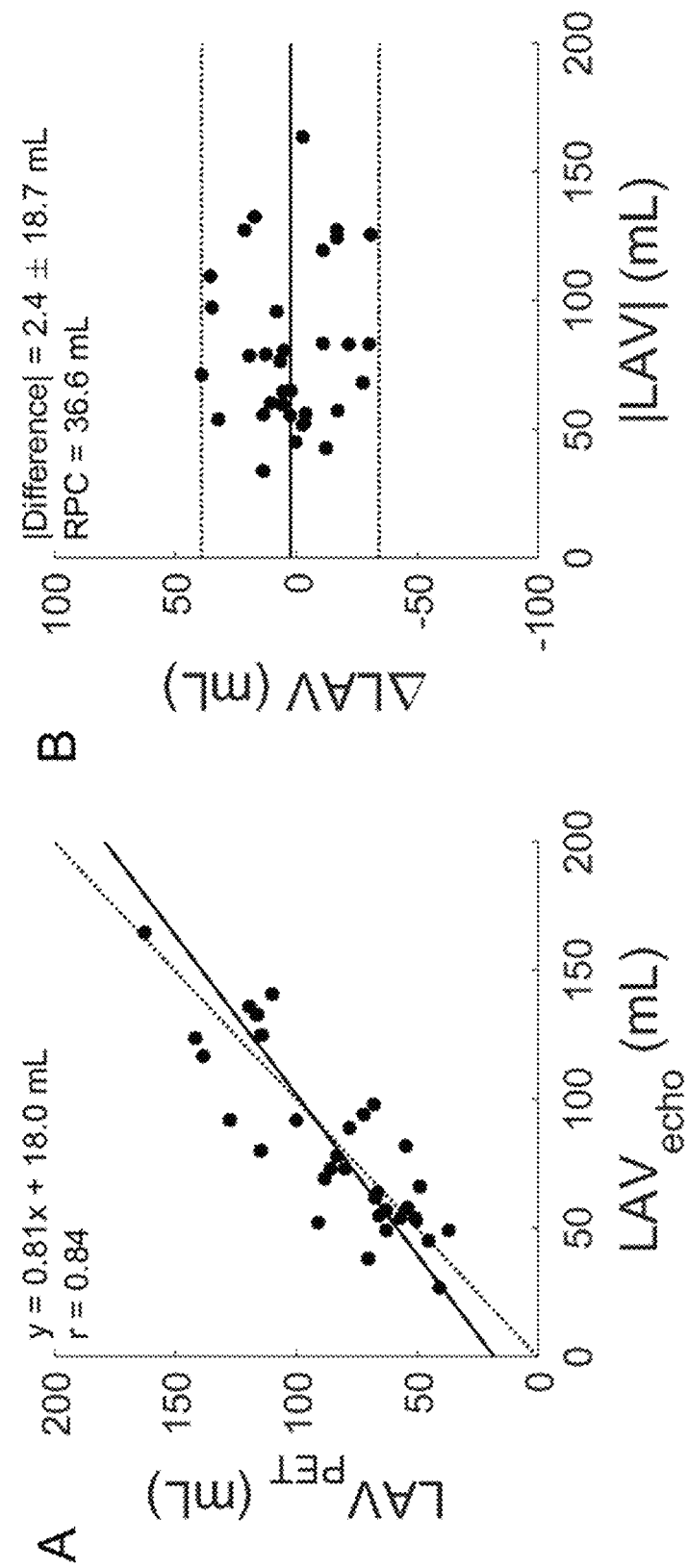
FIG. 7: Shows the high (r=0.84) correlation of PET-derived LA volume and echocardio-graphically-derived LA volume for HF patients.

FIG. 7: Shows the high (r=0.84) correlation of PET-derived LA volume and echocardio-graphically-derived LA volume for HF patients.

Figure 8:
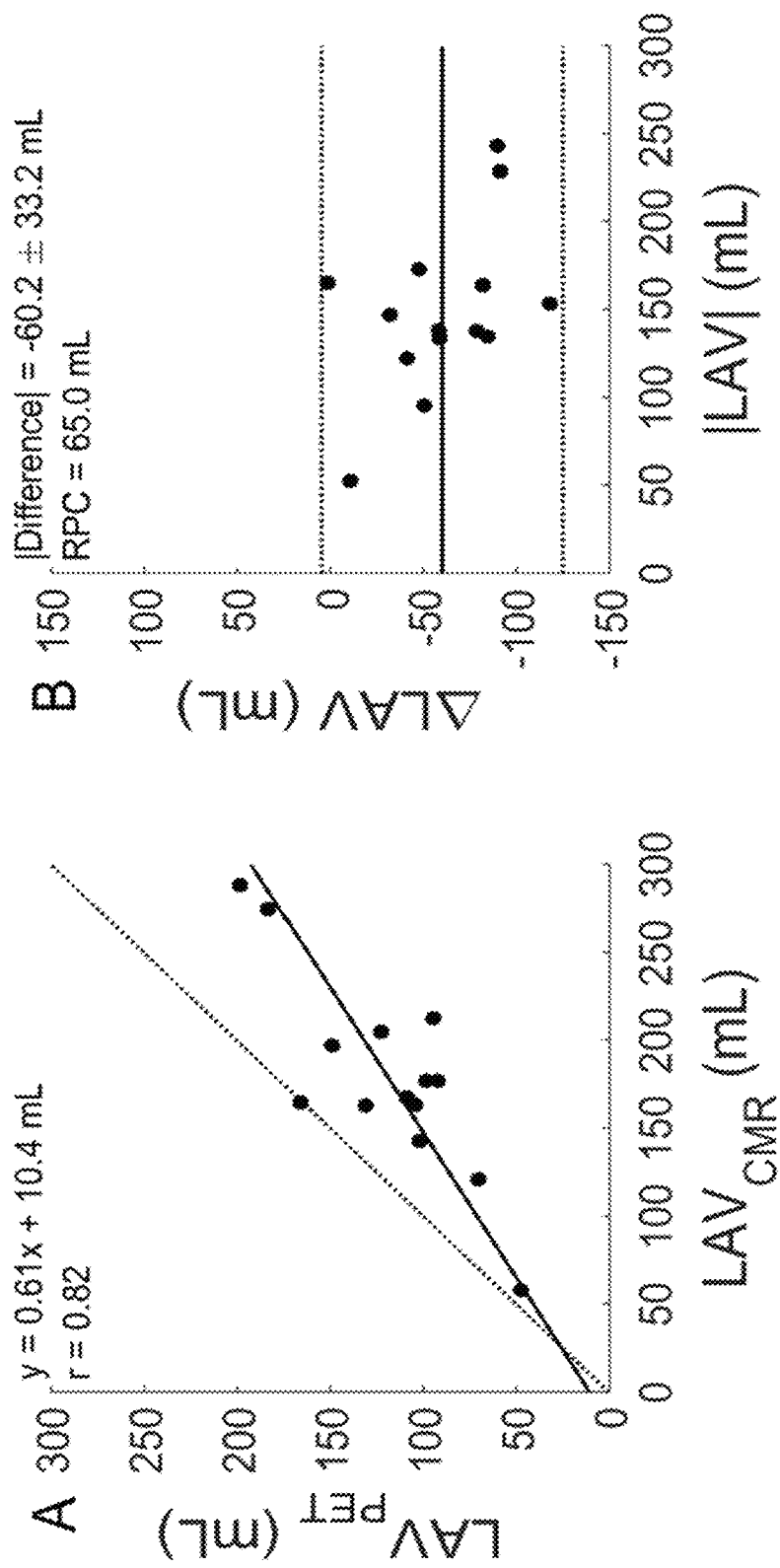
FIGS. 8 and 9: A comparison of PET with two different MRI measures, showing mean LA volume for PET but maximal LA volume for MRI.
Figure 9:
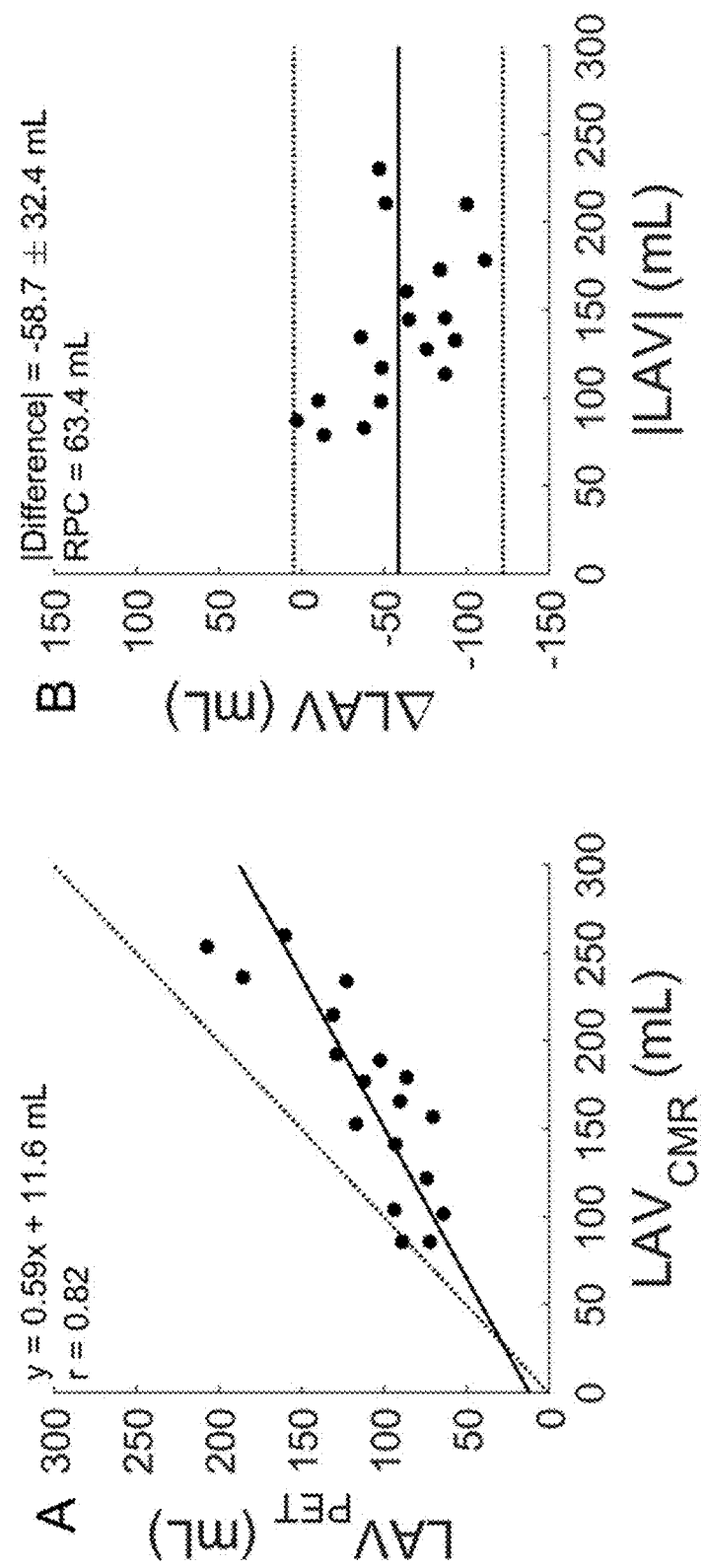

FIGS. 8 and 9: A comparison of PET with two different MRI measures, showing mean LA volume for PET but maximal LA volume for MRI.

Figure 10:
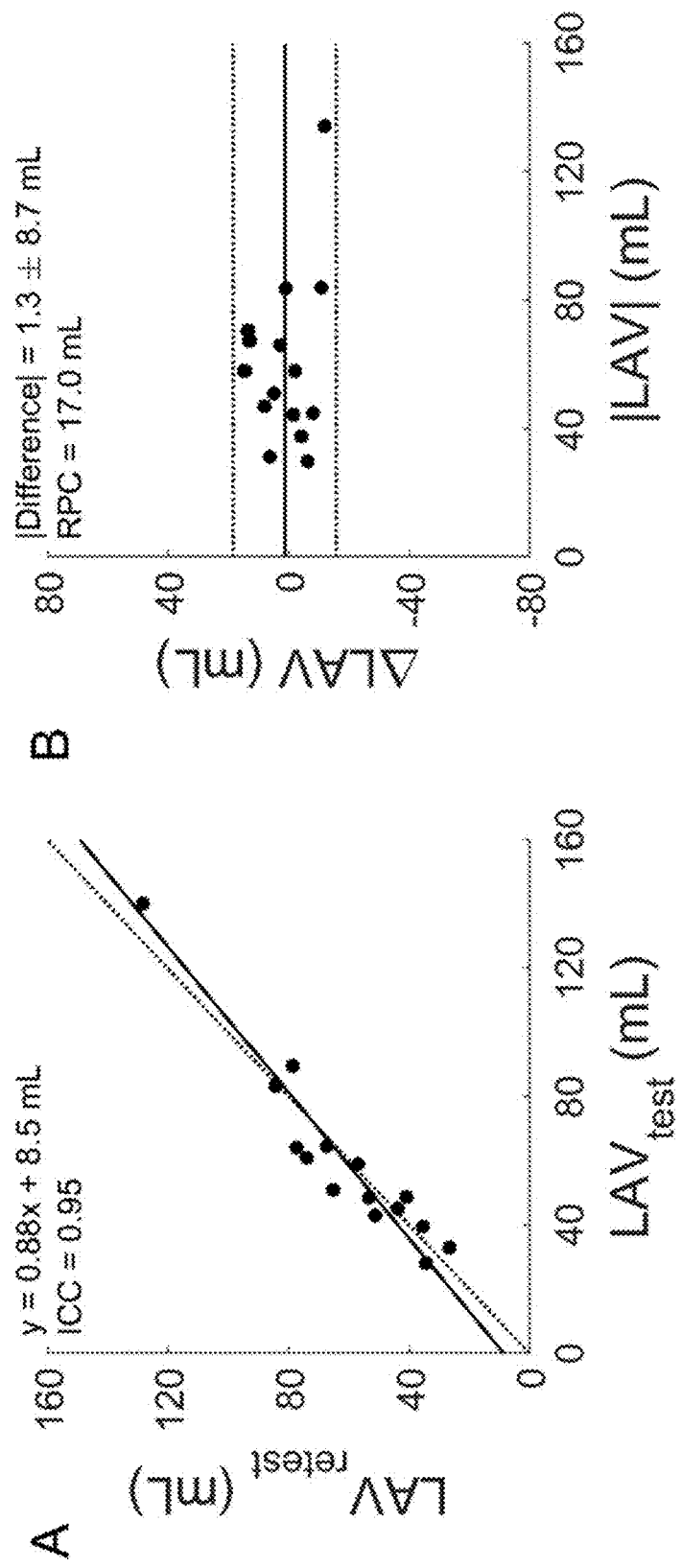
FIG. 10: Correlation (A) and Bland Altman (B) plot of test-retest reproducibility of LAVI.

FIG. 10: Correlation (A) and Bland Altman (B) plot of test-retest reproducibility of LAVI. Black and gray lines indicate the line of identity and the linear fit in (A) and the mean difference and the 95% confidence interval in (B). RPC: repeatability coefficient. The figure shows the high reproducibility of LA derived using PET when a patient is scanned twice (ICC=0.93 and a reproducibility coefficient of 8.6 mL/m$^2$).

Figure 11:
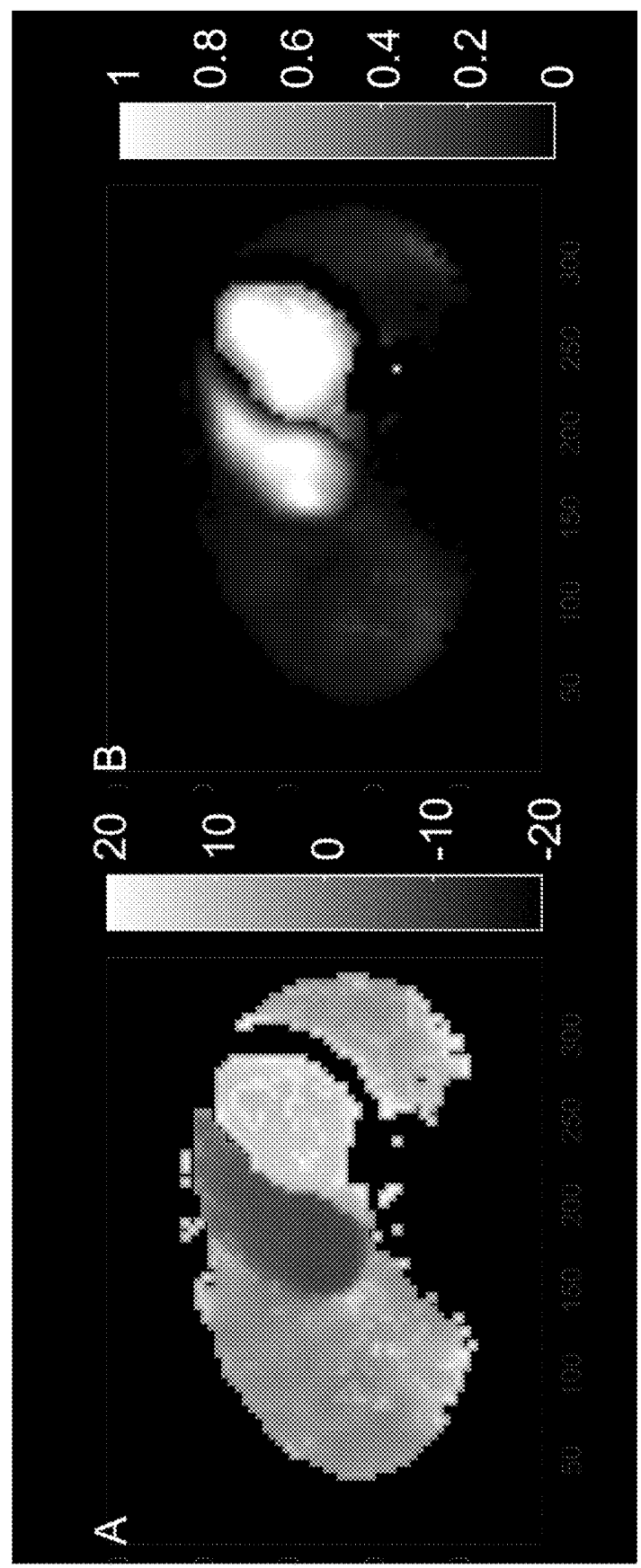
FIG. 11: Typical example of an image of bolus arrival time $t_{mid}$ (A), relative to that of the lungs, and area under curve AUC (B), normalized for the AUC of CLV(t).

FIG. 11: Typical example of an image of bolus arrival time $t_{mid}$ (A), relative to that of the lungs, and area under curve AUC (B), normalized for the AUC of $C_{LV}(t)$. For display purposes, regions with bolus arrival time more than 20 seconds after that of the left-ventricular cavity were removed from the images, effectively removing the non-blood regions.

Figure 12:
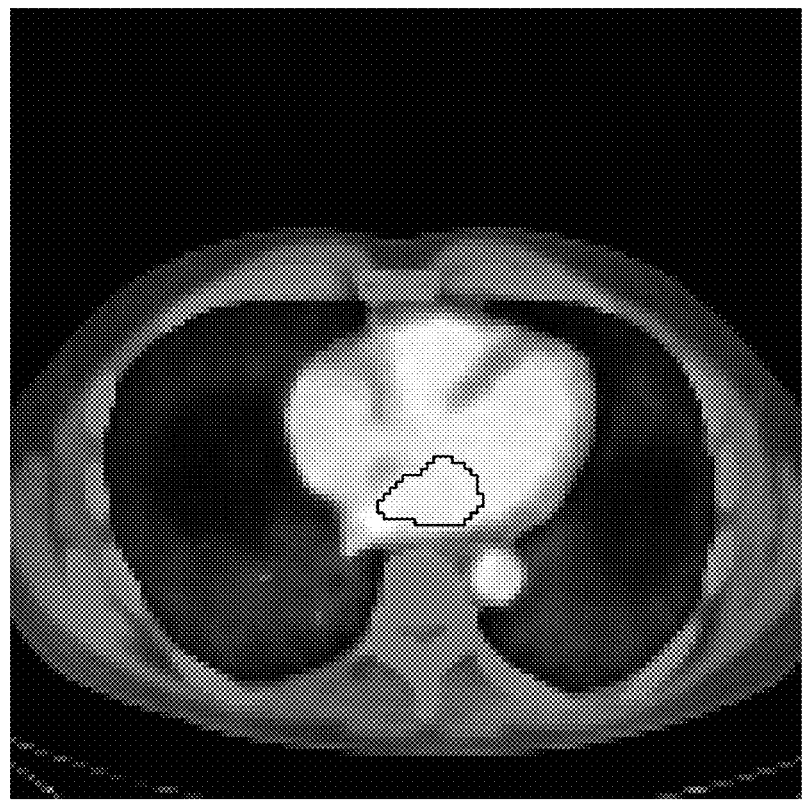
FIG. 12-14: Shows 3×2 images for patient scans. For each patient is included an image showing the area-under-curve images with the contours of the LA projected on them also projected onto a CT scan for anatomical reference. The patient scans are as follows.
Figure 13:
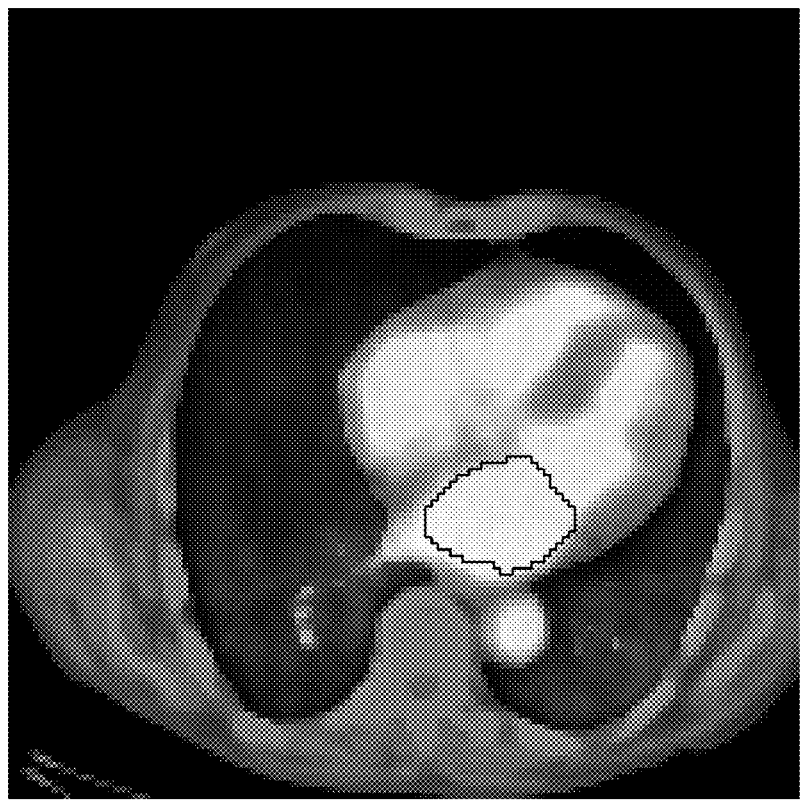
Figure 14:
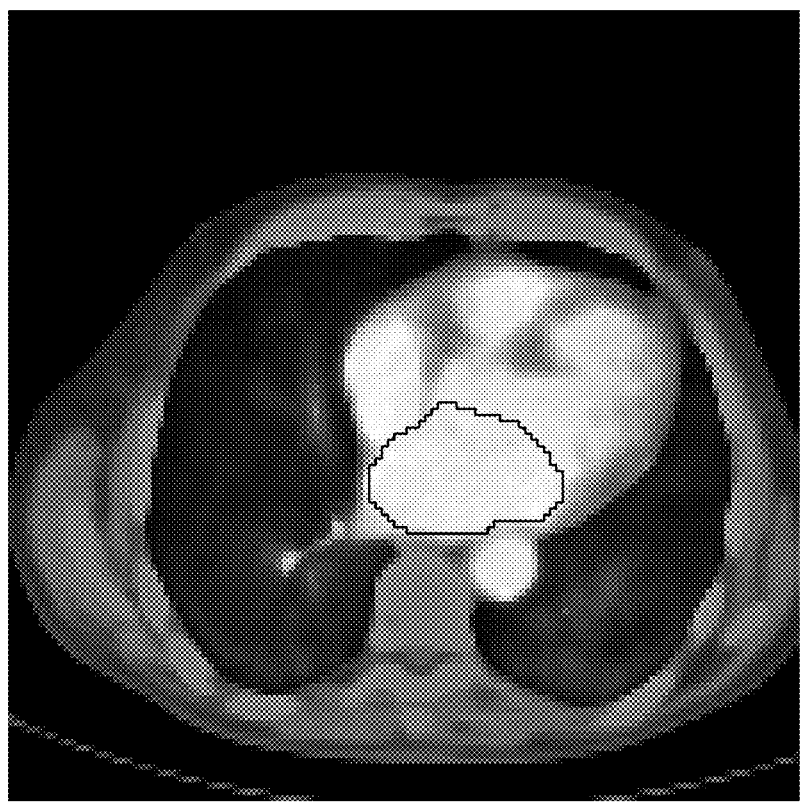

FIG. 12-14: Shows 3×2 images for patient scans. For each patient is included an image showing the area-under-curve images with the contours of the LA projected on them also projected onto a CT scan for anatomical reference. The patient scans are as follows:

FIG. 12: a healthy control, normal heart, normal (small) left atrium, everything normal.

FIG. 13: a patient suffering from amyloidosis. Such patients have a stiff heart (left-ventricle) that contracts normally but doesn't relax property, causing increased filling pressures and an overload of the LA, which leads to an enlarged LA as seen in the images. The LV itself is not enlarged.

FIG. 14: a patient with leaky valves—for each heartbeat, a significant amount of blood is pumped back through the leaky valves instead of through the aorta, resulting in ballooning of the left ventricle (to ensure enough blood goes into the aorta) and of course ballooning of the left atrium which is not accommodated to receive so much blood each heartbeat.

Figure 15:
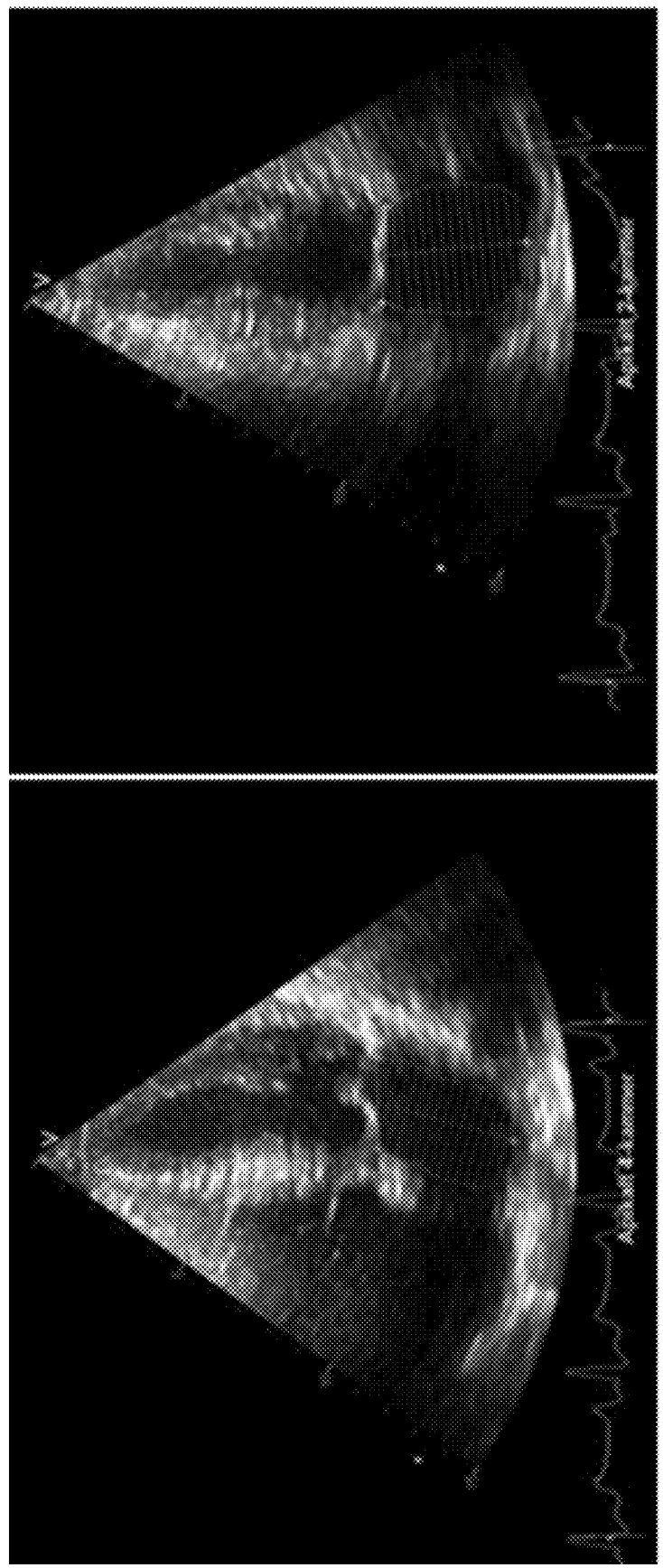
FIG. 15: Echocardiographic apical 4-chamber (left) and 2-chamber (right) views.

FIG. 15: Echocardiographic apical 4-chamber (left) and 2-chamber (right) views. The left atrium is manually traced in end-systole just before opening of the mitral valve.

Figure 16A:
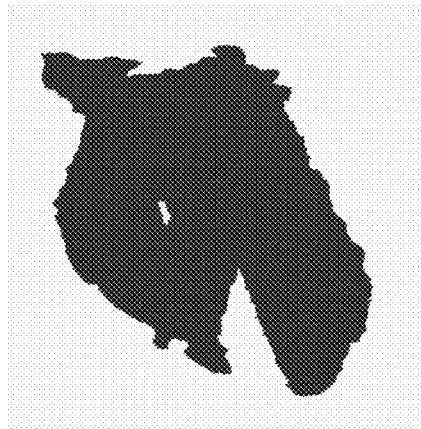
FIG. 16A-F: Shows how the mask used in the method according to the first preferred embodiment is developed.
Figure 16B:
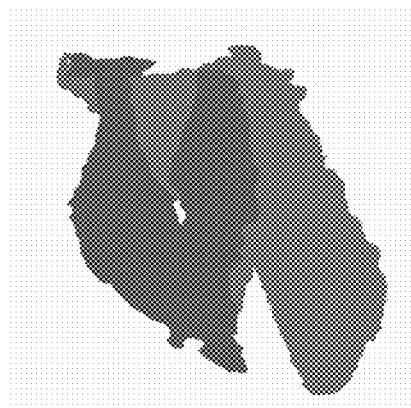
Figure 16C:
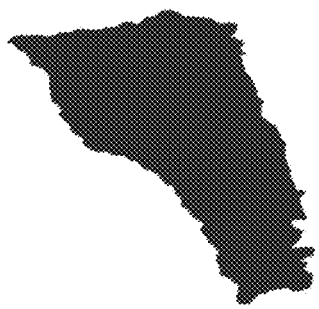
Figure 16D:
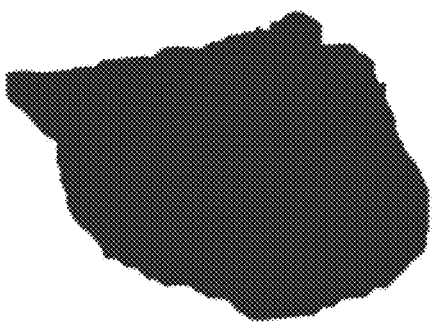
Figure 16E:
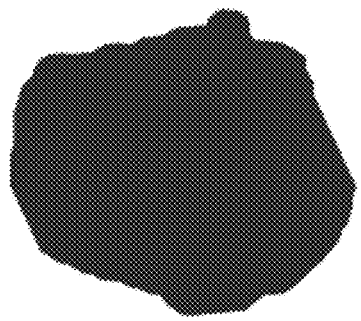
Figure 16F:
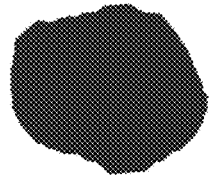

FIG. 16A-F: Shows how the mask used in the method according to the first preferred embodiment is developed. FIG. 16A shows the result after thresholding on the AUC (everything >⅔ of that of $AUC_{LV}$). FIG. 16B is the same mask as in FIG. 16A but separated using the mean centroid time of the LV and RV (i.e. after step g) vii) where we use the light grey colour for the left atrium and the dark grey for the right atrium. FIGS. 16C-16F focus on the left atrium. FIG. 16C corresponds to the light grey region of FIG. 16B (so >the mean of LV and RV centroids), after having removed all regions with centroid more than that of the LV+2 heartbeats. This removes the descending aorta from the images and most of the ascending aorta (after step g) viii). For the remaining three images, FIG. 16D shows the initial estimate after removing the LV cavity (step g) ix); FIG. 16E shows the mask after steps h) and i), and finally FIG. 16F shows the mask, that gives the final LA volume.

Figure 17A:
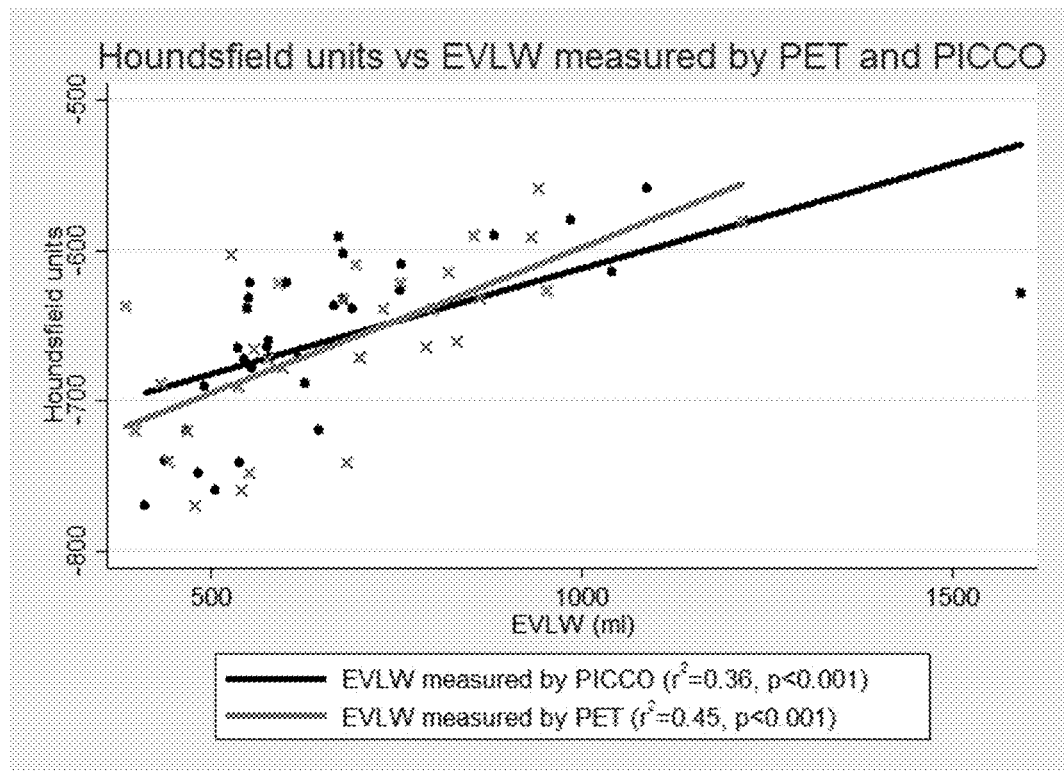
FIG. 17A shows the correlation between Houndsfield units (HU) and extravascular water content (EVLW).
Figure 17B:
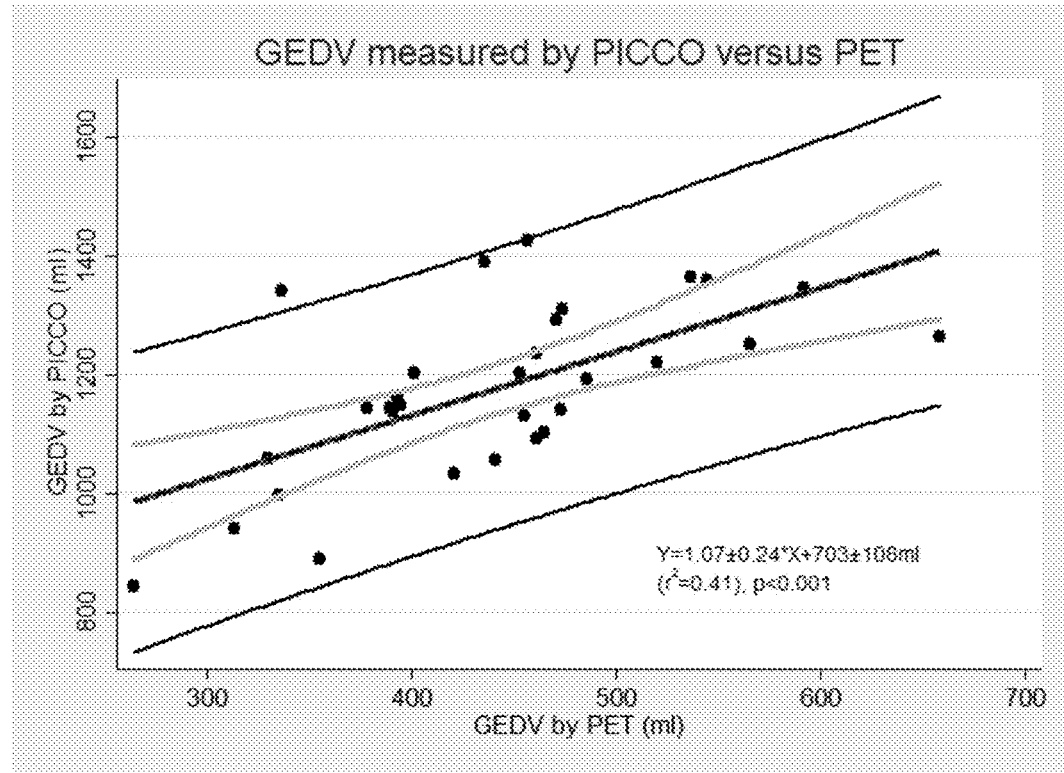
FIG. 17B shows the correlation between Global end-diastolic volume (GEDV) measured by PICCO and PET.

FIG. 17 A-B: FIG. 17A shows the correlation between Houndsfield units (HU) and extravascular water content (EVLW). EVLW correlated positively with HU measured with either PICCO ($r^2$=0.36) or PET ($r^2$=0.45). The correlation coefficient did not differ significantly between the two methods and HU (p=0.32). FIG. 17B shows the correlation between Global end-diastolic volume (GEDV) measured by PICCO and PET. GEDV measured with PICCO and PET correlated positively. (Grey lines depicts confidence interval and black lines predictive interval).

FIG. 18 Coronal CT scan of a pig at baseline (left) and the end of study (right), demonstrating the congestion evident by increased lung density (white areas).

Methods

The methods according to the first preferred embodiment as disclosed herein were validated by a comparison with either echocardiography (group 1) or cardiac magnetic resonance (CMR) imaging (group 2). Then, reproducibility was assessed in a test-retest setting (group 3). Additional data on accuracy and reproducibility was obtained using a different tracer. Finally, the new method was applied to a large cohort of patients (group 4) referred for standard clinical assessment of MBF.

Patient Population

The first group (HF) consisted of 36 patients with documented heart failure, which were part of a substudy of the LIVE study [Jorsal A at al. A protocol for a randomised, double-blind, placebo-controlled study of the effect of LIraglutide on left VEntricular function in chronic heart failure patients with and without type 2 diabetes (The LIVE Study). BMJ Open [Internet]. 2014; 4:e004885]. The second group (MR) consisted of 34 patients with mitral valvular regurgitation and mild to moderate (NYHA class I or II) heart failure. Group 3 (CAD) consisted of 15 patients referred for clinical evaluation of coronary artery disease. These patients underwent two $^{15}$O-water PET scans during rest on the same day. Finally, group 4 consisted of 107 patients with intermediate likelihood of coronary artery disease, referred for standard clinical evaluation of myocardial blood flow. HF patients were scanned at the Aarhus University Hospital, Aarhus, Denmark, whilst MR, CAD and clinical patients were scanned at the Uppsala University Hospital, Uppsala, Sweden.

Scanning Protocol

All studies were conducted on either a Siemens Biograph TruePoint TrueV 64 PET/CT scanner (HF patients), a GE discovery ST (20 MR patients, all CAD and clinical patients) or a GE Discovery MI (14 MR patients) with identical scanning protocols.

The methods according to the second preferred embodiment as disclosed herein included studying of eight anesthetized and ventilated pigs. Pulmonary congestion was induced by a combination of beta-blockers (BB), angiotensin-2 agonist (AT-2a) and saline infusion. Invasive pressure measurement, PICCO, computer tomography (CT) and $^{15}O$—$H_2O$-PET was performed.

Data Collection

Arterial blood pressure measurements, invasive hemodynamic by the Swan-Ganz catheter and PICCO examinations were performed at baseline as well as before and immediately after four PET (1: Before any intervention (BAL). 2: After initiation of AT2 and BB administration (AB), 3: again after 3 L of saline infusion (AB-3L), and finally, 4: after infusion of 10 L saline (AB-10L). Each examination block was separated by 1 hour.

Pulmonary Catheter Measurements

A Swan-Ganz catheter was inserted through a sheath placed in the internal jugular vein on the anterolateral part of the throat. A sheath was placed on the contralateral side to ensure sufficient vascular access. The Swan-Ganz pulmonary catheter technique allows for measurement and calculation of the following hemodynamic variables: Central venous pressure (CVP), pulmonary capillary wedge pressure (PCWP) and pulmonary artery pressure (PAP).

PICCO Measurements

PICCO (Pulsion Medical System, Maquet, Germany) measurements are based on transpulmonary thermodilution. A PICCO catheter was inserted through a sheath in the porcine femoral artery. 15 ml cooled saline (4 Celsius) was infused through a Swan-Ganz catheter at the level of the central venous access and the drop in temperature in arterial blood was measured. Cardiac output (CO), global end-diastolic volume (GEDV) and lung-water content (EVLW) were then estimated. Invasive blood pressure was measured through a sheath in the contralateral femoral artery and systemic vascular resistance (SVR) was calculated.

Computer Tomographic Examinations

The CT examinations were carried out on a Siemens Biograph 64 TruePoint PET/CT with TrueV, 120 kV, 1.0 mm slice thickness, 0.5 pitch, 350 mAs reference dose (Caredose) and a B31s filter. The examinations were performed during a breath hold at end-inspiration. The lungs were segmented using as previously described method (12). The mean lung density was calculated based on a volume of interest defined as all parenchymal tissue within the pleura with a Houndfield unit (HU) ranging from −900 to −350. CT-scans were carried out before and after each PET examination, and an average HU value for the entire lung was calculated at each stage (BAL-AB-AB3-AB10).

PET Examinations ($^{15}O$)—$H_2O$ $^{15}O$-water PET was performed according to standard clinical protocol. After performing a low-dose CT scan, 400 MBq of $^{15}O$-water dissolved in approximately 5 mL of saline was injected intravenously using an automated injection system (similarly as described in pending PCT application WO 2016/203055) at a speed of 2 mL/s, followed by a 35 mL saline flush. Simultaneously with tracer injection, a 10-minute acquisition protocol was started. Data were reconstructed as a dynamic scan using appropriate corrections for scatter, decay, attenuation and scanner normalization. Scanning was initiated prior to injection and continued for 10 minutes.

The invention claimed is:

1. A method for estimating the volume of an atrium (left (LA) or right (RA)) based on a plurality of emission tomography images, said method comprising the steps of:
   a) extracting time activity curves of an injected tracer for a plurality of pixels and/or voxels;
   b) isolating first-pass peaks of the time activity curves by
      i. detecting two or more successive frames $t_x$ to $t_{x+n}$ with the maximum downslope wherein x and n are both positive integers;
      ii. extrapolate the maximal downslope using $C_{PET}(t_x)$ and $C_{PET}(t_{x+n})$ in said successive frames using a fitting procedure;
      iii. defining the first-pass peak as the activity of the original $C_{PET}(t)$ up to $t_{x+n}$ followed by fitting of the downslope starting from the frames with maximal downslope;
   c) extracting the centroid-time of said first-pass peak $t_{mid}$ and the area under the curve AUC using the center of mass and total area, respectively, thereby affording a three-dimensional image for both $t_{mid}$ and for AUC,
   d) defining a ventricle using images showing high ventricle-to-blood contrast or late images of tracer retention,
   e) defining the ventricular cavity inside of the ventricular region,
   f) obtaining the cavity time-activity curve,
   g) extracting the first-pass peak,
   h) storing the resulting centroid, AUC and location of the ventricular cavity as $t_{mid}$ and AUC as $t_{LV}$, $t_{RV}$, $AUC_{LV}$ and $AUC_{RV}$,
   i) using $t_{mid}$ and AUC images, defining a mask as all regions with AUC higher than two thirds of $AUC_{LV}$,
   j) removing from said mask all regions either with
      for LA volume estimation
      iv. $t_{mid}$ less than $t_{LV}$ minus half of the difference between $t_{LV}$ and $t_{RV}$, or
      v. with $t_{mid}$ more than $t_{LV}$ plus the duration of two heartbeats, or
      vi. regions located within the LV cavity,
      vii. defining the center of gravity of the mask,
      viii. removing all regions in said mask more than 1 times the median distance from this center of gravity, or
      ix. eroding the resulting mask followed by a dilatation/expansion to remove thin tube-like regions,
      for RA volume estimation
      x. $t_{mid}$ more than $t_{LV}$ minus half of the difference between $t_{LV}$ and $t_{RV}$, or
      xi. with $t_{mid}$ more than $t_{RV}$ plus the duration of two heartbeats, or regions located within the RV cavity, or
      xii. regions depicting a vertical tube-like shape, by identifying the vertical slice with a significant increase in area of the mask for the slice as compared to the slice directly above,
   k) using the total volume of the remaining mask as an estimate of mean LA or RA volume.

2. A method according to claim 1 wherein the atrium for which the volume is estimated is the left atrium (LA).

3. A method according to claim 1 wherein the atrium for which the volume is estimated is the right atrium (RA).

4. A method according to claim 1 wherein the center of mass is calculated as $$t_{mid} = \frac{\Sigma C_{first\ pass}(t) \cdot frame\ duration}{\Sigma C_{first\ pass}(t)}$$

and the total area is calculated as AUC=$\Sigma C_{first\ pass}$(t)·frame duration, respectively.

5. A method according to claim 1 wherein the plurality of emission tomography images is generated by a method selected from:
Computer tomography, using time frames separated by 0.5-10 seconds and a scanning time of 10-120 seconds,
CMR, using time frames separated by 0.1-10 seconds and a scanning time of 10-120 seconds,
Single photon emission tomography (SPECT/gamma camera) as long as said isotope-molecule ligand is not retained in lung tissue during the first pass through the lungs after injection, using time frames separated by 3-10 seconds and a scanning time of 10-120 seconds, or
PET with any PET-amenable radioisotope, as long as said isotope and the labeled molecule is not retained in lung tissue during the first pass through the lungs after injection, using time frames separated by 1-10 seconds and a scanning time of 10-120 seconds.

6. The method according to claim 1, which is based on dynamic MBF PET scans.

7. The method according to claim 1, wherein the tracer has been injected in a vein entering the right atrium of the heart.

8. The method according to claim 1, wherein the tracer that has been injected is a bolus of radio-opaque contrast media, wherein the first-pass peak of each time activity curves corresponds to the bolus arriving at the pixel/voxel.

9. The method according to claim 1, wherein the tracer is selected from $^{11}$C-acetate and $^{15}$O-water, preferably $^{15}$O-water.

10. A method for identifying a cardiac disease by analyzing the estimated volumes of the left or right atrium obtained by the method according to claim 1.

11. A non-transitory computer readable storage medium containing computer executable instructions that, when executed by a processor, cause said processor to execute or perform the method according to claim 1.

12. A system for estimating the volume of the left or right atrium of a human heart based on a plurality of emission tomography images of said human heart, said system comprising a processor arranged to perform the method according to claim 1.

13. The method according to claim 1, wherein the plurality of emission tomography images comprise positron emission tomography images or single-photon emission computed tomography images.

14. The method according to claim 1, wherein the fitting procedure comprises exponential fitting, linear fitting or gamma-function fitting.

15. The method according to claim 1, wherein the images showing high ventricle-to-blood contrast comprise parametric images generated using basis function methods.

16. The method according to claim 1, wherein, for LA volume estimation, removing all regions in said mask more than 1.5 times the median distance from this center of gravity.

17. The method according to claim 1, wherein, for LA volume estimation, eroding the resulting mask followed by a dilatation/expansion to remove pulmonary veins.

18. The method according to claim 1, wherein, for RA volume estimation, removing from said mask regions depicting a vena cava by identifying the vertical slice with a 50% increase in area of the mask for the slice as compared to the slice directly above.

19. The method according to claim 5, wherein the plurality of emission tomography images is generated by computer tomography with intravenous injection of iodinated contrast media, using time frames separated by 0.5-10 seconds and a scanning time of 30-60 seconds.

20. The method according to claim 5, wherein the plurality of emission tomography images is generated by CMR with gadolinium-based contrast media, using time frames separated by 0.1-10 seconds and a scanning time of 30-60 seconds.

21. The method according to claim 5, wherein the plurality of emission tomography images is generated by single photon emission tomography (SPECT/gamma camera) with a SPECT-amendable radioisotope linked with any molecule, as long as said isotope-molecule ligand is not retained in lung tissue during the first pass through the lungs after injection, using time frames separated by 3-10 seconds and a scanning time of 30-60 seconds.

22. The method according to claim 5, wherein the plurality of emission tomography images is generated by PET using time frames separated by 1-10 seconds and a scanning time of 30-60 seconds.

23. The system according to claim 12 further comprising: an emission imaging device arranged to provide the emission tomography images.

24. The method according to claim 12, wherein the plurality of emission tomography images comprise positron emission tomography images or single-photon emission computed tomography images.

\* \* \* \* \*